United States Patent
Sears et al.

(10) Patent No.: US 11,730,774 B2
(45) Date of Patent: Aug. 22, 2023

(54) BACTERIAL BIOFILMS AND CANCER

(71) Applicant: THE JOHNS HOPKINS UNIVERSITY, Baltimore, MD (US)

(72) Inventors: Cynthia L. Sears, Baltimore, MD (US); Christine Craig, Baltimore, MD (US); Drew M. Pardoll, Brookeville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/976,721

(22) PCT Filed: Feb. 28, 2019

(86) PCT No.: PCT/US2019/020161
§ 371 (c)(1),
(2) Date: Aug. 28, 2020

(87) PCT Pub. No.: WO2019/169202
PCT Pub. Date: Sep. 6, 2019

(65) Prior Publication Data
US 2020/0405779 A1    Dec. 31, 2020

Related U.S. Application Data

(60) Provisional application No. 62/636,777, filed on Feb. 28, 2018.

(51) Int. Cl.
*A61K 35/741* (2015.01)
*A61P 35/00* (2006.01)
*C12Q 1/689* (2018.01)
*G01N 33/569* (2006.01)

(52) U.S. Cl.
CPC ............ *A61K 35/741* (2013.01); *A61P 35/00* (2018.01); *C12Q 1/689* (2013.01); *G01N 33/56916* (2013.01)

(58) Field of Classification Search
None
See application file for complete search history.

(56) References Cited

U.S. PATENT DOCUMENTS 4,522,811 A    6/1985   Eppstein et al.
6,468,798 B1  10/2002   Debs et al.

FOREIGN PATENT DOCUMENTS

WO    2010115092 A3    3/2011
WO    2011146910 A1   11/2011
WO    2015038731 A1    3/2015

OTHER PUBLICATIONS

Viljoen etal (PLOS One, 10(3) e0119462, 2015, pp. 1-21).*
McGhee and Fujihashi 2012; Inside the Mucosal Immune System. PLoS Biol 10, e1001397.
Lied G A, Berstad A.: 48. Functional and clinical aspects of the Bcell-activating factor (BAFF): a narrative review. Scand J Immunol. Jan. 2011; 73(1):1-7.
Cancro M P: The BLyS family of ligands and receptors: an archetype for niche-specific homeostatic regulation. Immunol Rev. Dec. 2004; 202:237-49.
Tertilt C, Joh J, Krause A, et al. Expression of B-cell activating factor enhances protective immunity of a vaccine against Pseudomonas aeruginosa. Infect Immun. 2009;77(7):3044-3055. doi:10.1128/IAI. 00927-08.
E. R. Fearon, B. Vogelstein, Cell 61, 759-767 (1990).
Giardiello FM, Krush AJ, Petersen GM, et al. Phenotypic variability of familial adenomatous polyposis in 11 unrelated families with identical APC gene mutation. Gastroenterology. 1994; 106(6):1542-1547. doi:10.1016/0016-5085(94)90408-1.
C. Dejea, E. Wick, C. L. Sears, Future Microbiol. 8, 445-460 (2013).
Swidsinski A, Loening-Baucke V, Theissig F, et al. Comparative study of the intestinal mucus barrier in normal and inflamed colon. Gut. 2007;56(3):343-350. doi:10.1136/gut.2006.098160.
A. Swidsinski, V. Loening-Baucke, A. Herber, J. Physiol. Pharmacol. 60 (Suppl 6), 61-71 (2009).
Dejea CM, Wick EC, Hechenbleikner EM, et al. Microbiota organization is a distinct feature of proximal colorectal cancers. Proc Natl Acad Sci U S A. 2014;111(51):18321-18326. doi:10.1073/pnas. 1406199111.
Johnson CH, Dejea CM, Edler D, et al. Metabolism links bacterial biofilms and colon carcinogenesis. Cell Metab. 2015;21(6):891-897. doi:10.1016/j.cmet.2015.04.011.
Son JS, Khair S, Pettet DW 3rd, et al. Altered Interactions between the Gut Microbiome and Colonic Mucosa Precede Polyposis in APCMin/+ Mice. PLoS One. 2015;10(6):e0127985. Published Jun. 29, 2015. doi:10.1371/journal.pone.0127985.
Wu S, Rhee KJ, Albesiano E, et al. A human colonic commensal promotes colon tumorigenesis via activation of T helper type 17 T cell responses. Nat Med. 2009;15(9):1016-1022. doi:10.1038/nm. 2015.
Arthur JC, Perez-Chanona E, Muhlbauer M, et al. Intestinal inflammation targets cancer-inducing activity of the microbiota. Science. 2012;338(6103):120-123. doi:10.1126/science.1224820.
Prindiville TP, Sheikh RA, Cohen SH, Tang YJ, Cantrell MC, Silva J Jr. Bacteroides fragilis enterotoxin gene sequences in patients with inflammatory bowel disease. Emerg Infect Dis. 2000;6(2):171-174. doi:10.3201/eid0602.000210.
Prorok-Hamon M, Friswell MK, Alswied A, et al. Colonic mucosa-associated diffusely adherent afaC+ *Escherichia coli* expressing lpfA and pks are increased in inflammatory bowel disease and colon cancer. Gut. 2014;63(5):761-770. doi:10.1136/gutjnl-2013-304739.
Boleij A, Hechenbleikner EM, Goodwin AC, et al. The Bacteroides fragilis toxin gene is prevalent in the colon mucosa of colorectal cancer patients. Clin Infect Dis. 2015;60(2):208-215. doi:10.1093/cid/ciu787.

(Continued)

*Primary Examiner* — Brian Gangle
(74) *Attorney, Agent, or Firm* — Fox Rothschild LLP

(57) ABSTRACT

Compositions for the treatment of colorectal cancer target bacterial biofilms in the gastrointestinal tract. Methods of treatment include one or more agents which target bacteria and the bacterial biofilms.

14 Claims, 27 Drawing Sheets

(56) References Cited

OTHER PUBLICATIONS

Martinez-Medina M, Mora A, Blanco M, et al. Similarity and divergence among adherent-invasive *Escherichia coli* and extraintestinal pathogenic *E. coli* strains. J Clin Microbiol. 2009;47(12):3968-3979. doi:10.1128/JCM.01484-09.

Ma C, Dong X. Colorectal cancer-derived Foxp3(+) IL-17(+) T cells suppress tumour-specific CD8+ T cells. Scand J Immunol. 2011;74(1):47-51. doi:10.1111/j.1365-3083.2011.02539.x.

Pankey GA, Sabath LD. Clinical relevance of bacteriostatic versus bactericidal mechanisms of action in the treatment of Gram-positive bacterial infections. Clin Infect Dis. 2004;38(6):864-870. doi:10.1086/381972.

Nicolaou, K. C.; Li, T.; Nakada, M.; Hummel, C. W.; Hiatt, A.; Wrasidlo, W. Calicheamicin A Rationally Designed Molecule with Extremely Potent and Selective DNA Cleaving Properties and Apoptosis Inducing Activity. Angew. Chem. Int. Ed. Engl. 1994, 33, 183-186.

\* cited by examiner

**Presence of *pks+ E. coli* and ETBF on colon mucosa of FAP patients and Controls**

| | Total | *pks+ E. coli* | ETBF | *pks+ E. coli, ETBF* | Neither |
|---|---|---|---|---|---|
| FAP | 25 | 17 (68%) | 15 (60%) | 13 (52%) | 6 (24%) |
| Controls | 23 | 5 (22%) | 7 (30%) | 5 (22%) | 16 (70%) |
| p value | | 0.002 | 0.049 | 0.0400 | 0.0030 |

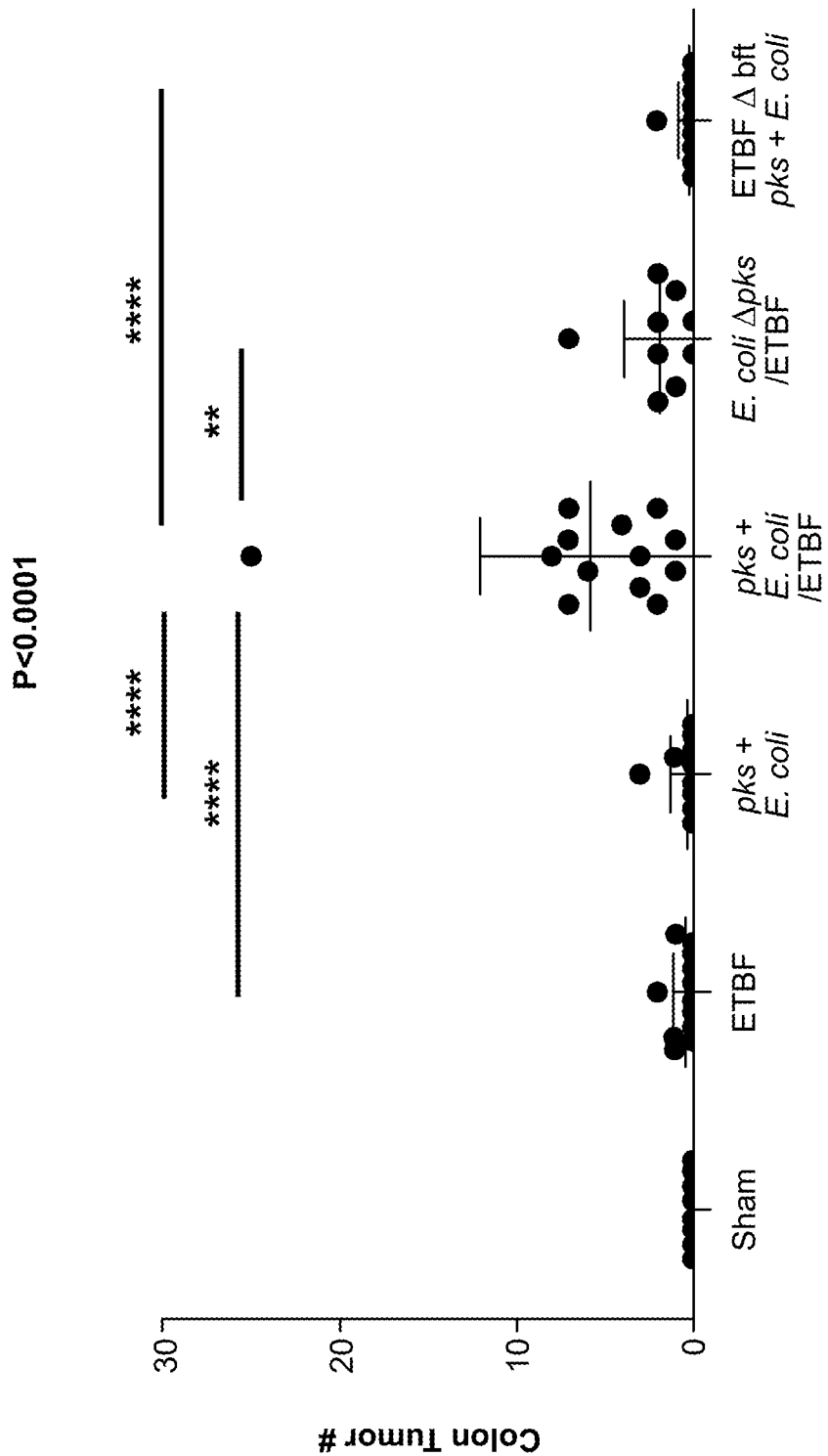

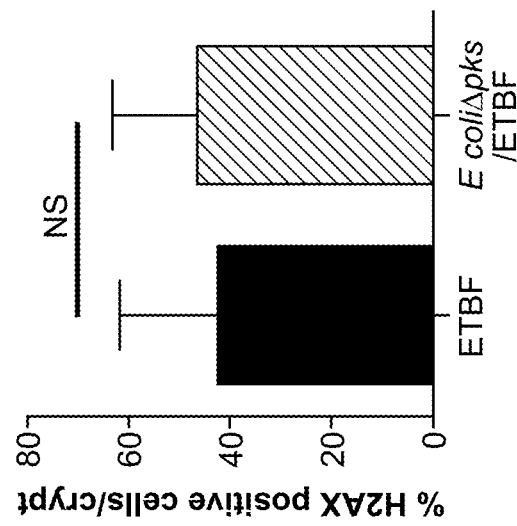
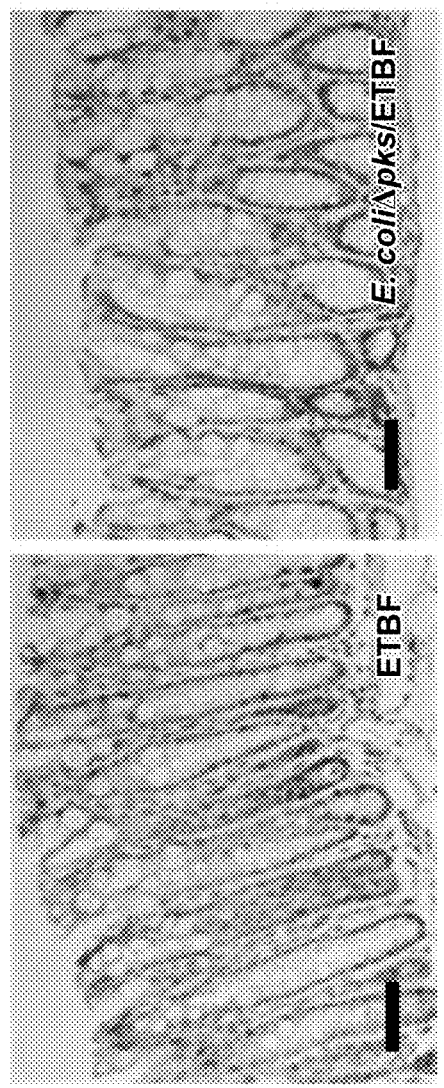
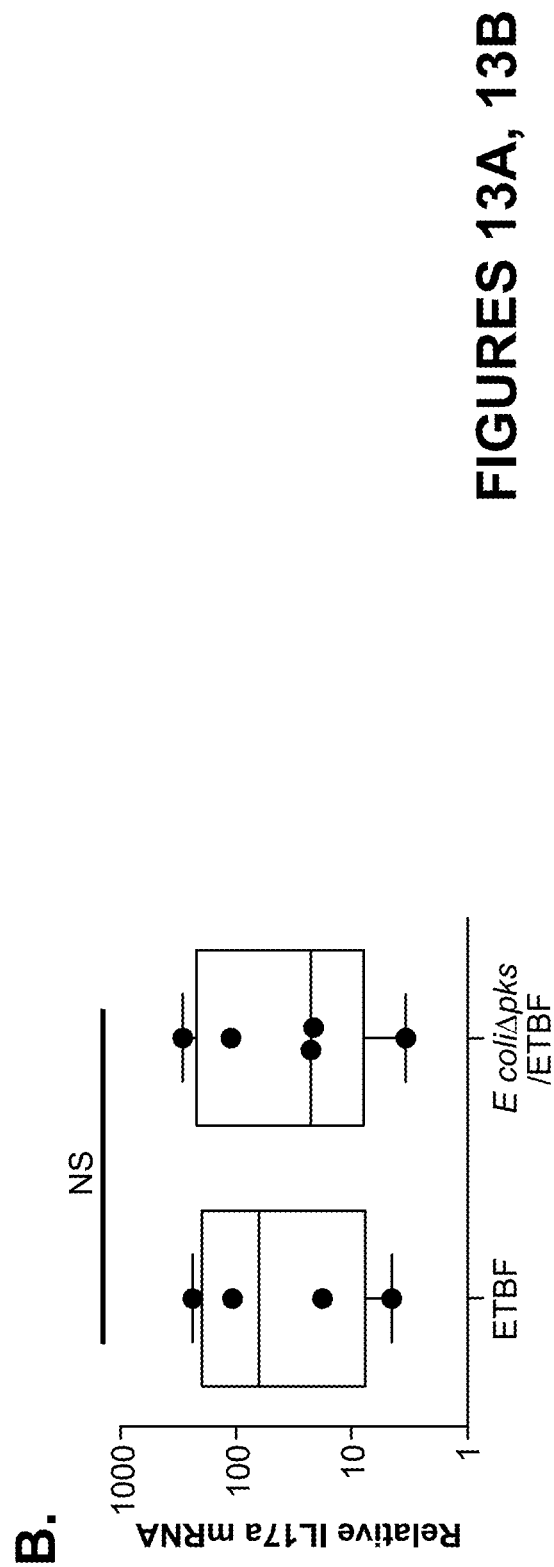
FIGURES 13A, 13B

BACTERIAL BIOFILMS AND CANCER

CROSS REFERENCE TO RELATED APPLICATIONS

This Application is a national stage of application filed under 35 U.S.C. § 371 of International Application No. PCT/US2019/020161, filed Feb. 28, 2019, which claims the benefit of U.S. Provisional Application 62/636,777 filed on Feb. 28, 2018, the entire contents of which, are incorporated herein by reference in their entirety.

GOVERNMENT SUPPORT

This invention was made with government support under Grant No.: CA151393 awarded by the National Institutes of Health. The government has certain rights in the invention.

FIELD OF THE INVENTION

Embodiments of the invention are directed to treatment of cancer and/or diseases associated with bacterial biofilm formation.

BACKGROUND

Colorectal cancer (CRC) is very common globally and develops through accumulation of colonic epithelial cell (CEC) mutations that promote transition of normal mucosa to adenocarcinoma. Around 5% of CRC occurs in individuals with an inherited mutation (1). One hereditary condition, familial adenomatous polyposis (FAP), is caused by germ-line mutation in the APC tumor suppressor gene. Individuals with FAP are born with their first mutation in the transition to CRC, and as somatic mutations accumulate, develop hundreds to thousands of colorectal polyps. The onset and frequency of polyp formation within families bearing the same APC gene mutation varies substantially (2), suggesting that additional factors contribute to disease onset, including components of the microbiome (3).

The colon contains trillions of bacteria that are separated from the colonic epithelium by a dense mucus layer. This mucus layer promotes tolerance to foreign antigens by limiting bacterial—epithelial cell contact and, thus, mucosal inflammatory responses. In contrast, bacterial breaches into the colonic mucus layer with, in some, bio-film formation fosters chronic mucosal inflammation (4-6).

SUMMARY

Embodiments of the invention are directed to treatment of colorectal cancer by therapeutic compositions which target bacterial biofilms in the gastrointestinal tract.

In one aspect, there is provided a method for treating colorectal cancer (CRC) in a subject, comprising administering a therapeutically effective amount of one or more agents which are bactericidal, bacteriostatic and/or inhibit growth or activity of bacteria in a bacterial biofilm in the subject's gastrointestinal tract, wherein the bacterial biofilm comprises at least one bacterial type from *Bacteroides* and at least one bacterial type from Enterobacteriaceae. In certain embodiments, the method of treating a subject suffering from colorectal cancer includes administration of one or more chemotherapeutic or immunotherapeutic agents.

In a second aspect, there is provided a composition for preventing or treating colorectal cancer where the composition comprises a therapeutically effective amount of one or more antibacterial/antimicrobial agents, small molecule inhibitors, vaccines and/or one or more probiotics, wherein the antibacterial agents are bactericidal and/or bacteriostatic for enterotoxigenic *Bacteroides fragilis* (ETBF) and *Escherichia coli* (*E. coli*). In certain embodiments, the composition comprises one or more probiotics and/or chemotherapeutic agents.

In a third aspect, there is provided a method of preventing colorectal cancer or treating a subject for colorectal cancer, comprising administering to the subject an antimicrobial agent and/or probiotic, wherein colibactin (clbB) and *Bacteroides fragilis* toxin (bft), are detected in mucosa of a subject's gastrointestinal tract. In certain embodiments, the antibacterial/antimicrobial agents inhibit: growth, activity or are bactericidal to bacteria, comprising enterotoxigenic *Bacteroides fragilis* (ETBF) and/or *Escherichia coli* (*E. coli*).

In a fourth aspect, there is provided a method of treating a neoplastic condition in a subject comprising (i) detecting a bacterial biofilm within the gastrointestinal tract of a subject; and (ii) administering an antimicrobial agent or a probiotic agent to the subject in an amount effective to reduce the size of the bacterial biofilm. In certain embodiments, the bacterial biofilm is detected within the colon of the subject and comprises enterotoxigenic *Bacteroides fragilis* (ETBF) and *Escherichia coli* (*E. coli*). In certain embodiments, the ETBF and/or *E. coli* are detected by one or more assays comprising in situ hybridization, blotting, polymerase chain reaction (PCR), immunoassays, reporter assays, or any combinations thereof. In some embodiments, the bacterial biofilm is positive for colibactin (clbB) and *Bacteroides fragilis* toxin (bft).

In a fifth aspect, there is provided a kit for detecting enterotoxigenic *Bacteroides fragilis* (ETBF) and *Escherichia coli* (*E. coli*) comprises a synthetic oligonucleotide conjugated to a detectable label, wherein the synthetic oligonucleotide specifically hybridizes to *Bacteroides fragilis* or *Bacteroides fragilis* toxin (bft); and, a synthetic oligonucleotide conjugated to a detectable label, wherein the synthetic oligonucleotide specifically hybridizes to *Escherichia coli* or colibactin (clbB). In the alternative, the kit comprises one or more antibodies or agents which specifically bind to one or more antigenic epitopes of ETBF and/or *E. coli*. The antibodies or agents, e.g. aptamers, can be conjugated to a detectable label. The kit can also include one or more buffers, pharmaceutical excipients, saline, distilled water or combinations thereof.

Other aspects are described infra.

Definitions

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "adjuvant" refers to any substance that can stimulate an immune response (e.g., a mucosal immune response). Some adjuvants cause activation of a cell of the immune system (e.g., an adjuvant can cause an immune cell to produce and secrete a cytokine). Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, immunogenic compositions described herein are administered with one or more adjuvants (e.g., to skew the immune response towards a Th1 and/or Th2 type response).

As used herein, the term "agent" or "antibacterial agent" or "antimicrobial agent" is meant to encompass any molecule, chemical entity, composition, drug, therapeutic agent, chemotherapeutic agent, or biological agent capable of preventing, ameliorating, or treating the diseases or other medical conditions or bacterial infections. The term includes small molecule compounds, small molecule inhibitors, antisense oligonucleotides, antibiotics, species-specific bacteriophages, small molecule inhibitors of toxins, vaccines, toxins, membrane destabilizing agents, antibacterial or antimicrobial compounds, siRNA reagents, antibodies, antibody fragments bearing epitope recognition sites, such as Fab, Fab', F(ab')2 fragments, Fv fragments, single chain antibodies, antibody mimetics (such as DARPins, affibody molecules, affilins, affitins, anticalins, avimers, fynomers, Kunitz domain peptides and monobodies), peptoids, aptamers; cytokines, cellular factors, enzymes, immune cell modulating agents, adoptive cell therapeutics, peptides, organic or inorganic molecules, natural or synthetic compounds and the like. An agent can be assayed in accordance with the methods of the invention at any stage during clinical trials, during pre-trial testing, or following FDA-approval.

As used herein, the term "antibiotic" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria. Non-limiting exemplary antibiotics include those classified as aminoglycosides, beta-lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics. The term also includes antimicrobial agents isolated from natural sources or chemically synthesized. The term "antibiotic" also refers to antimicrobial agents for use in human therapy. Exemplary antibiotics include: tetracyclines, fluoroquinolones, chloramphenicol, penicillins, cephalosporins, puromycin, nalidixic acid, and rifampin. Additional specific examples of antibiotics include clindamycin, carbenicillin, cefoperazone, cefamandole, sulfonamides, quinolones, oxazolidinones, carbapenems, aminoglycosides, erythromycin, tetracycline and sulbactam. The term also includes pharmacologically acceptable sodium salts, pharmacologically acceptable calcium salts, pharmacologically acceptable potassium salts, lipid formulations, derivatives and/or analogs of the above.

The phrase "anti-biofilm formation activity" as used herein refers to the capacity of a substance to effect the prevention of formation of a biofilm of bacterial, fungal and/or other cells; and/or to effect a disruption and/or the eradication of an established and/or matured biofilm of bacterial, fungal and/or other cells; and/or to effect a reduction in the rate of buildup of a biofilm of bacterial, fungal and/or other cells on a surface (e.g., within the gastrointestinal tract of a subject).

The phrase "anti-biofilm formation compound/composition/agent" as used herein refers to a substance having an anti-biofilm formation activity, as defined herein.

As used herein, the term "antimicrobial" refers to a property of a substance (e.g., a compound or a composition) that can effect a parameter of a microorganism, including death, eradication, elimination, reduction in number, reduction of growth rate, inhibition of growth, change in population distribution of one or more species of microbial life forms. This term encompasses antibacterial agents and antibiotics.

An "antimicrobial agent", as used herein, refers to an agent that is capable of decreasing or eliminating or inhibiting the growth of microorganisms such as that term is known in the art (exemplary microorganisms include microbes such as bacteria, fungi, viruses and other pathogens).

As used in the context of embodiments of the present invention, the phrase "antimicrobial effective amount" describes an amount of an antimicrobial agent which will effect one or more parameters of a microorganism, including death, eradication, elimination, reduction in number, reduction of growth rate, inhibition of growth, change in population distribution of one or more species of microbial life forms, as described herein. In some embodiments, an antimicrobial effective amount is an amount that reduces to some extent the population of a microorganism in a biofilm structure and/or within the gastrointestinal tract of a subject.

The term "bacteriostatic" as used herein, means that the agent prevents the growth of bacteria (i.e., it keeps them in the stationary phase of growth). The term "bactericidal" means that the agent kills bacteria. Agents that are called "bactericidal" usually fail to kill every organism (if, for instance, the inoculum is large) within 18-24 hr, and most "bacteriostatic" agents kill some bacteria within 18-24 hr—often more than 90%-99% of the inoculum, but not enough (>99.9%) to be called "bactericidal." The in vitro microbiological determination of whether an antibacterial agent is bactericidal or bacteriostatic may be influenced by growth conditions, bacterial density, test duration, and extent of reduction in bacterial numbers. Most antibacterials are better described as potentially being both bactericidal and bacteriostatic. (G. A. Pankey and L. D. Sabath. *Clinical Infectious Diseases*, Volume 38, Issue 6, 15 Mar. 2004, Pages 864-870). Various in vitro microbiological techniques to determine the bactericidal activity of antibacterial agents against different isolates include the minimum bactericidal concentration (MBC), time-kill curve, and serum bactericidal titer (SBT).

The term "biofilm" as used herein refers to an aggregate of bacterial microorganisms in which bacterial cells adhere to each other and/or to a surface. These adherent cells are often covered with a matrix of extracellular polymeric substance (EPS), which is produced by the cells and/or host. Biofilm EPS has been characterized as composed of extracellular DNA, proteins, and polysaccharides. Such biofilms may form on any living or non-living surfaces, in particular both on solid surfaces as colonies and/or on liquid surfaces as pellicles. Microbial cells growing in a biofilm are physiologically distinct from planktonic cells of the same organism. In certain aspects of the invention, bacterial formations within the gastrointestinal tract of a subject are defined as biofilms if such formations are of a minimal size. In particular, exemplified biofilms were characterized as a massive bacterial invasion (>$10^9$ bacteria/ml) of the mucus layer spanning at least a linear distance of 200 μm of the epithelial surface; however, as described in greater detail below, a range of bacterial density and/or size cutoffs may be selected as defining a biofilm within a subject.

By "cancer" or "proliferative disease" as used herein is meant, a disease, condition, trait, genotype or phenotype characterized by unregulated cell growth or replication as is known in the art; including colorectal cancer, as well as, for example, leukemias, e.g., acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of its environment (e.g., treating the environment with an antibiotic effective against a bacterial bioform), alone or in combination with other therapies.

As used herein, the term "cancer therapy" refers to a therapy useful in treating cancer. Examples of anti-cancer therapeutic agents include, but are not limited to, antibacterial agents as described herein as well as, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN™), anti-CD20 antibodies, an epidermal growth factor receptor (EGFR) antagonist (e.g., a tyrosine kinase inhibitor), HER1/EGFR inhibitor (e.g., erlotinib (TARCEVA™)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein. The term "cancer therapy", as used herein, includes the antimicrobial agents and probiotic agents of the instant invention, as well as art-recognized forms of treating neoplastic conditions.

A "chemotherapeutic agent" is a chemical compound useful in the treatment of cancer.

As used herein, the term "compound" refers to small molecules. Examples of such small molecules would include low molecular weight molecules. Other examples of compounds include molecules that are generated by organic synthesis, and low molecular weight molecules that are metabolites or anti-metabolites.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used herein, the term "effective amount" refers to the amount of a therapy that is sufficient to result in therapeutic benefit to a patient with cancer, In one embodiment, the cancer patient has been diagnosed with a biofilm and, optionally, with CRC. In one embodiment, the effective amount is administered to a patient that has been diagnosed with cancer. The effective amount can result in the prevention of the development, recurrence, or onset of cancer and one or more symptoms thereof, to enhance or improve the efficacy of another therapy, reduce the severity, the duration of cancer, ameliorate one or more symptoms of cancer, prevent the advancement of cancer, cause regression of cancer, and/or enhance or improve the therapeutic effect(s) of another therapy. "Effective amount" also refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three, or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, (12) an increase in the number of patients in remission, (13) an increase in the length or duration of remission, (14) a decrease in the recurrence rate of cancer, (15) an increase in the time to recurrence of cancer, and (16) an amelioration of cancer-related symptoms and/or quality of life.

As used herein, the term "enhanced immunity" refers to an increase in the level of adaptive and/or acquired immunity in a subject to a given immunogen (e.g., microorganism (e.g., pathogen)) following administration of a composition relative to the level of adaptive and/or acquired immunity in a subject that has not been administered the composition.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL™, Bristol-Myers Squibb). Paclitaxel and docetaxel promote the assembly of microtubules from tubulin dimers and stabilize microtubules by preventing depolymerization, which results in the inhibition of mitosis in cells.

As used herein, the term "immune response" refers to any detectable response by the immune system of a subject. For example, immune responses include, but are not limited to, an alteration (e.g., increase) in Toll receptor activation, lymphokine (e.g., cytokine (e.g., Th1 or Th2 type cytokines) or chemokine) expression and/or secretion, macrophage activation, dendritic cell activation, T cell (e.g., CD4+ or CD8+ T cell) activation, NK cell activation, and/or B cell activation (e.g., antibody generation and/or secretion). Additional examples of immune responses include binding of an immunogen (e.g., antigen (e.g., immunogenic polypeptide)) to an MHC molecule and induction of a cytotoxic T lymphocyte ("CTL") response, induction of a B cell response (e.g., antibody production), and/or T-helper lymphocyte response, and/or a delayed type hypersensitivity (DTH) response (e.g., against the antigen from which an immunogenic polypeptide is derived), expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to an antigen and/or immunogen (e.g., both the initial response to an immunogen (e.g., a pathogen) as well as acquired (e.g., memory) responses that are a result of an adaptive immune response). As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route. As used herein, the term "under conditions such that said subject generates an immune response" refers to any qualitative or quantitative induction, generation, and/or stimulation of an immune response (e.g., innate or acquired).

As used herein, the term "immunity" refers to protection from disease (e.g., preventing or attenuating (e.g., suppression of) a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the terms "immunogen", "immunogenic" and "antigen" are used interchangeably to refer to an agent (e.g., a microorganism (e.g., bacterium, virus or fungus) and/or portion or component thereof (e.g., a protein antigen)) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention. As used herein, the terms "*Bacteroides*" and "Enterobacteriaceae" antigens refers to a component or product of a bacteria of the genus *Bacteroides*" or "Enterobacteriaceae" that elicits an immune response when administered to a subject. An antigen may be a component or product derived from an organism (e.g., bacteria of the genus *Bacteroides* or Enterobacteriaceae) including, but not limited to, polypeptides, peptides, proteins, nucleic acids, membrane fractions, and polysaccharides.

"Mucosal immunity" or the "mucosal immune system" (MIS), can be separated into inductive and effector sites based upon their anatomical and functional properties. The migration of immune cells from mucosal inductive to effector tissues via the lymphatic system is the cellular basis for the immune response in the GI, the UR, and female reproductive tracts. Mucosal inductive sites include the gut-associated lymphoid tissues (GALT) and nasopharyngeal-associated lymphoid tissues (NALT), as well as less well characterized lymphoid sites. Collectively, these comprise a mucosa-associated lymphoid tissue (MALT) network for the provision of a continuous source of memory B and T cells that then move to mucosal effector sites. The MALT contains T cell regions, B cell—enriched areas harboring a high frequency of surface IgA-positive (sIgA$^+$) B cells, and a subepithelial area with antigen-presenting cells (APCs), including dendritic cells (DCs) for the initiation of specific immune responses. The MALT is covered by a subset of differentiated microfold (M) cells, ECs, but not goblet cells, and underlying lymphoid cells that play central roles in the initiation of mucosal immune responses. M cells take up antigens (Ags) from the lumen of the intestinal and nasal mucosa and transport them to the underlying DCs. The DCs carry Ags into the inductive sites of the Peyer's patch or via draining lymphatics into the mesenteric lymph nodes (MLNs) for initiation of mucosal T and B cell responses. Retinoic acid (RA) producing DCs enhance the expression of mucosal homing receptors ($\alpha 4\beta 7$ and CCR9) on activated T cells for subsequent migration through the lymphatics, the bloodstream, and into the GI tract lamina propria. Regulation within the MIS is critical; several T cell subsets including $T_H 1$, $T_H 2$, $T_H 17$, and $T_{regs}$ serve this purpose.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, "neoplasia" means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Colon cancer (e.g., colorectal cancer), lung cancer and ovarian cancer are examples (non-limiting) of a neoplastic condition.

As used in this specification and the appended claims, the term "or" is generally employed in its sense including "and/or" unless the content clearly dictates otherwise.

By "reduce or inhibit" is meant the ability to cause an overall decrease of 20% or greater, or 50% or greater, or 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

By "subject" or "patient" is meant an organism to which the methods of the invention can be applied and/or to which the agents of the invention can be administered. A subject can be a mammal, including a human, or a mammalian organ or mammalian cells, including a human organ and/or human cells.

Certain methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

As used herein, a "tissue sample" refers to a portion, piece, part, segment, or fraction of a tissue which is obtained or removed from an intact tissue of a subject, preferably a human subject. In one embodiment, the tissue sample is a gastrointestinal tract sample, optionally a colorectal sample.

"Treatment", or "treating" as used herein, is defined as the application or administration of a therapeutic agent or combination of therapeutic agents (e.g., an antimicrobial agent and, optionally, another cancer preventing and/or therapeutic agent (e.g., chemotherapeutic)) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, a "tumor sample" refers to a portion, piece, part, segment, or fraction of a tumor, for example, a tumor which is obtained or removed from a subject (e.g., removed or extracted from a tissue of a subject), preferably a human subject.

As used herein, the terms "prevent," "preventing" and "prevention" in the context of the administration of a therapy to a subject refer to the prevention or inhibition of the recurrence, onset, and/or development of a cancer or a symptom thereof in a subject resulting from the administration of a therapy (e.g., a prophylactic agent), or a combination of therapies (e.g., a combination of prophylactic agents). In some embodiments, such terms refer to one, two, three, or more results following the administration of one or more therapies: (1) a stabilization, reduction or elimination in the cancer cell population, (2) an increase in response rate, (3) an increase in the length or duration of remission, (4) a decrease in the recurrence rate of cancer, (5) an increase in the time to recurrence of cancer, (6) an increase in the disease-free, relapse-free, progression-free, and/or overall survival of the patient, and (7) an amelioration of cancer-related symptoms and/or quality of life. In specific embodiments, such terms refer to a stabilization, reduction or elimination of the cancer stem cell population.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

BRIEF DESCRIPTION OF THE FIGURES

FIG. 1A the top panels show representative FISH images of bacterial biofilms (red) on the mucosal surface of a FAP polyp and paired normal tissues counterstained with DAPI (4',6-diamidino-2-phenylindole) nuclear stain (blue). Middle panels show that most of the biofilm composition was identified as $B.\ fragilis$ (green) and $E.\ coli$ (red) by using species-specific probes. The bottom panels show the PAS (periodic acid— Schiff)—stained histopathology images of polyp and paired normal mucosal tissues demonstrating the presence of the mucus layer. Images were obtained at 40× magnification; scale bars, 50 μm. Dotted lines delineate the luminal edge of the colonic epithelial cells. Images are representative of n=4 to 23 tissue samples per patient screened (at least 10 5-μm sections screened per patient). FIG. 1B shows Enterobacteriaceae (yellow) and $E.\ coli$ (red) FISH probes on paired normal FAP tissue (100× magnification) revealing invasion into the epithelial cell layer at the base of a crypt. Bottom panels with insets of Enterobacteriaceae (bottom left panel) in yellow, $E.\ coli$ (bottom middle panel) in red, and overlay (bottom right panel) confirming identification of the invasive species. Scale bar, 20 μm. Images are representative of n=5 to 16 tissue samples per patient screened (at least 10 5 μm sections screened per patient). FIG. 1C shows the FAP and control prevalence of pks+ $E.\ coli$ and enterotoxigenic $Bacteroides\ fragilis$ (ETBF). Chi-square P-values are shown that represent the difference in probability of detection of each bacterium in FAP versus control patients. FIG. 1D shows the PCR detection of clbB (a gene in the pks island) and bft within laser-captured biofilms containing $E.\ coli$ and $B.\ fragilis$ from designated FAP patients (Table 1) and controls (Table 2; materials and methods). Data show a representative image from two independent experiments with two or three replicates per experiment performed.

FIGS. 2A-2D show that co-colonization by pks+ $E.\ coli$ and ETBF increases colon tumor onset and mortality in murine models of CRC. FIG. 2A depicts total colon tumor numbers detected in sham (n=9), ETBF mono-colonized (n=12), pks+ $E.\ coli$ mono-colonized (n=11), pks+ $E.\ coli$/ETBF co-colonized (n=13), $E.\ coli$Δpks/ETBF (n=9), or pks+ $E.\ coli$/ETBFΔbft (n=10) AOM mice at 15 weeks after colonization. Data indicate mean±SEM. Overall significance was calculated with the Kruskal-Wallis test, and the overall P value is shown; Mann-Whitney U was used for two-group comparisons; P=0.016, **P<0.0001. FIG. 2B depicts representative colons of mono-colonized (ETBF or pks+ $E.\ coli$), co-colonized (ETBF/pks+ $E.\ coli$), $E.\ coli$Δpks/ETBF, and pks+ $E.\ coli$/ETBFΔbli mice at 15 weeks after colonization of AOM-treated mice. Images are representative of n=9 to 13 mice for each group. FIG. 2C shows the H&E (hematoxylin and eosin) histopathology of an invasive adeno-carcinoma in a cocolonized (pks+ $E.\ coli$/ETBF) AOM mouse at 15 weeks. Main image, 10× magnification; scale bar, 1 mm. Inset image, 100× magnification; scale bar, 0.2 mm. Blue arrow depicts the disruption of the muscularis propria by the invasive adenocarcinoma, and white arrows (inset) identify invading clusters of adenocarcinoma epithelial cells. FIG. 2D is a Kaplan-Meir survival plot of Apc$^{\Delta716Min/+}$ mice (n=30) colonized with either ETBF (blue; n=10), pks+ E. coli (orange; n=10), or cocolonized with pks+ E. coli and ETBF (purple; n=10). Co-colonization significantly (P<0.0001) increased the mortality rate. Statistics were analyzed with the log-rank test. All surviving mice (n=19) were harvested at 110 days.

(FIG. 3A) Histologic hyperplasia and (FIG. 3B) inflammation scores of 15-week AOM sham (n=9), ETBF monocolonized (n=12), pks+ E. coli monocolonized (n=11), or pks+ E. coli/ETBF cocolonized (n=13) mice. Data represent mean±SEM of three independent experiments. For FIGS. 3A and 3B, overall significance was calculated by using the Kruskal-Wallis test, and the overall P value is shown; Mann-Whitney U was used for two-group comparisons; P=0.01, *P=0.0014, ****P=0.0006; NS, not significant. FIG. 3C: Myeloid and lymphoid lamina propria immune cell infiltrates plotted as percentage of live cells in AOM mice at day 7 (top panels) and day 21 (bottom panels) after colonization. Data represent mean±SEM of three independent experiments (total three to five mice per group). FIG. 3D shows the total tumor numbers detected in IL-17—deficient AOM-treated mice (IL17$^{-/-}$) versus wild-type AOM mice (WT). Both mouse strains were cocolonized with pks+ E. coli and ETBF and tumors assessed at 15 weeks. Data represent mean±SEM of two or three independent experiments (total 6 to 13 mice per group). Significance calculated by the Mann-Whitney U test represents differences between the non-normally distributed colon tumors in the independent mouse groups. FIG. 3E: IL-17— producing cell subsets and total number of T cells per colon harvested from germ-free C57BL/6 mice monocolonized with pks+ E. coli or ETBF or cocolonized with pks+ E. coli and ETBF for up to 60 hours. Data represent mean±SEM of two independent experiments (total 3 to 5 mice per group). Overall significance across IL-17—producing cell types was calculated by using two-way analysis of variance testing based on log-transformed data (bold P value). For each cell subset and total number of T cells (gray dotted line box), the overall P value is shown and was calculated by using the Kruskal-Wallis test. Two-group cell subset and total number of T cell comparisons were analyzed by Mann-Whitney U test and are reported in Table 7

FIG. 4A: ELISA results showing anti-pks+ E. coli (NC101) IgA and anti-ETBF (86-5443-2-2) IgA present in fecal supernatants from wild-type AOM mice under the designated colonization conditions for 4 weeks. Data represent mean±SEM of three independent experiments (total 3 to 10 mice per group). FIG. 4B shows the colonization of distal colon mucosae by pks+ E. coli and ETBF under mono- and co-colonization conditions at 4 weeks in AOM mice. Data represent mean of three independent experiments (total of 15 mice per group) FIG. 4C: Mucus depth (μm) of HT29-MTX-E12 monolayers under the designated colonization conditions. Data represent mean±SEM of three independent experiments. A. muc. Akkermansia muciniphila. FIG. 4D shows representative images of γ-H2AX immunohistochemistry of distal colon crypts from AOM mice (five mice per condition) mono- or co-colonized with pks+ E. coli and ETBF for 4 days with quantification (right panel) of γ-H2AX-positive cells displayed as percentage positive per crypt (see material and methods). Data represent mean±SEM of three independent experiments. For FIGS. 4A, 4B and 4D, significance was calculated with the Mann-Whitney U test for two-group comparisons; for FIG. 4C, overall significance was calculated with the Kruskal-Wallis test and the overall P value is shown. Mann-Whitney U was used for two-group comparisons; ****P<0.0001.

FIGS. 13A and 13B show H2AX analysis and IL17a qPCR of E. coli Δpks mouse colon in AOM mice. Colonic epithelial cell DNA damage was not enhanced in co-colonized E. coliΔpks/ETBF mice at day 4 after bacterial inoculation and administration of AOM. FIG. 13A: H2AX immunohistochemical staining of distal colon (left) and quantification (right) in mice mono-colonized with ETBF and co-colonized with E. coli Δpks/ETBF. Data (right) represent mean+/−SEM. FIG. 13B: Mucosal IL17A is similar in mono-colonized ETBF and co-colonized E. coli Δpks/ETBF mice. Data represent box-and-whisker plot (line, median; box, interquartile range; whiskers, $10^{th}$ and $90^{th}$ percentiles). Results represent one independent experiment (total 4 mice per group). Significance was calculated using the Mann-Whitney U test.

FIG. 14A: Colon tumor counts in mice mono-colonized with pks+ E. coli or A muciniphila or co-colonized with A. muciniphila/pks+ E. coli. Overall significance was calculated using the Kruskal-Wallis test and the overall p value is shown; Mann-Whitney U was used for two group comparisons, p value: *, p<0.05. FIG. 14B:=Detection of pks+ E. coli or A. muciniphila by fecal qPCR. Dotted line reflects limit of fecal detection ($10^2$ gene copies for pks+ E. coli and $10^2$ gene copies for A. muciniphila). Data represent mean+/−SEM of 2 independent experiments (total 5-9 mice per group).

FIG. 15A: Myeloid cell gating strategy; (1) Dendritic cells (DC) are identified as $CD11c^+IA/E^+$ after gating out dead cells (viable cell gate). (2) Macrophages are identified from the viable cell gate as $F4/80^+$ $CD64^+$. (3) Monocytes are identified from the $CD11b^+$ gate as $Ly6C^{hi}Ly6G^-$. (4) Neutrophils are identified from the $CD11b^+$ gate as $Ly6C^+Ly6G^+$. FIG. 15B: Lymphoid cell gating strategy; (1) $CD4^+$ T cells are identified as $CD3^+$ $CD4^+$ after gating out dead cells (viable cell gate). (2) $CD8^+$ T cells are identified from the viable cell gate as $CD3^+CD8^+$. (3) γδT cells are identified from the viable cell gate as $CD3^+γδTCR^+$. (4) B cells are identified from the viable cell gate as $CD3^-CD19^+$. FIG. 15C: Intracellular Cytokine Staining to detect IL-17-producing cells; (1) $IL-17^+$ total cells are identified as $CD45^+$ after gating out dead cells, viable B cells and neutrophils (viable $CD19^-GR1^-$ gate). (2) IL-17-producing innate lymphoid cells ($IL-17^+$ ILC) are identified from the viable $CD45^+$ cell gate as $IL-17^+CD3^-$ $Thy1.2^+$. (3) IL-17-producing $CD4^+$ cells (Th17) are identified from the $CD3^+Thy1.2+$ gate as $IL-17^+CD4^+Foxp3^-$. (4) γδT17 cells are identified from the $CD4-Foxp3^-$ T cell gate as $IL-17^+γδ$ from the $TCR^+$. (5) IL-17-producing cytotoxic T cells (Tc17) are identified from the $CD4^-Foxp3^-$ T cell gate as $IL-17^+γδTCR-CD8β^+$. (6) IL-17-producing natural killer cells ($IL-17^+$-NKT cells) are identified from $CD4-Foxp3^-$ T cell gate as $IL-17^+γδTCR-CD8β^-$.

DETAILED DESCRIPTION

Figures 1A, 1B:
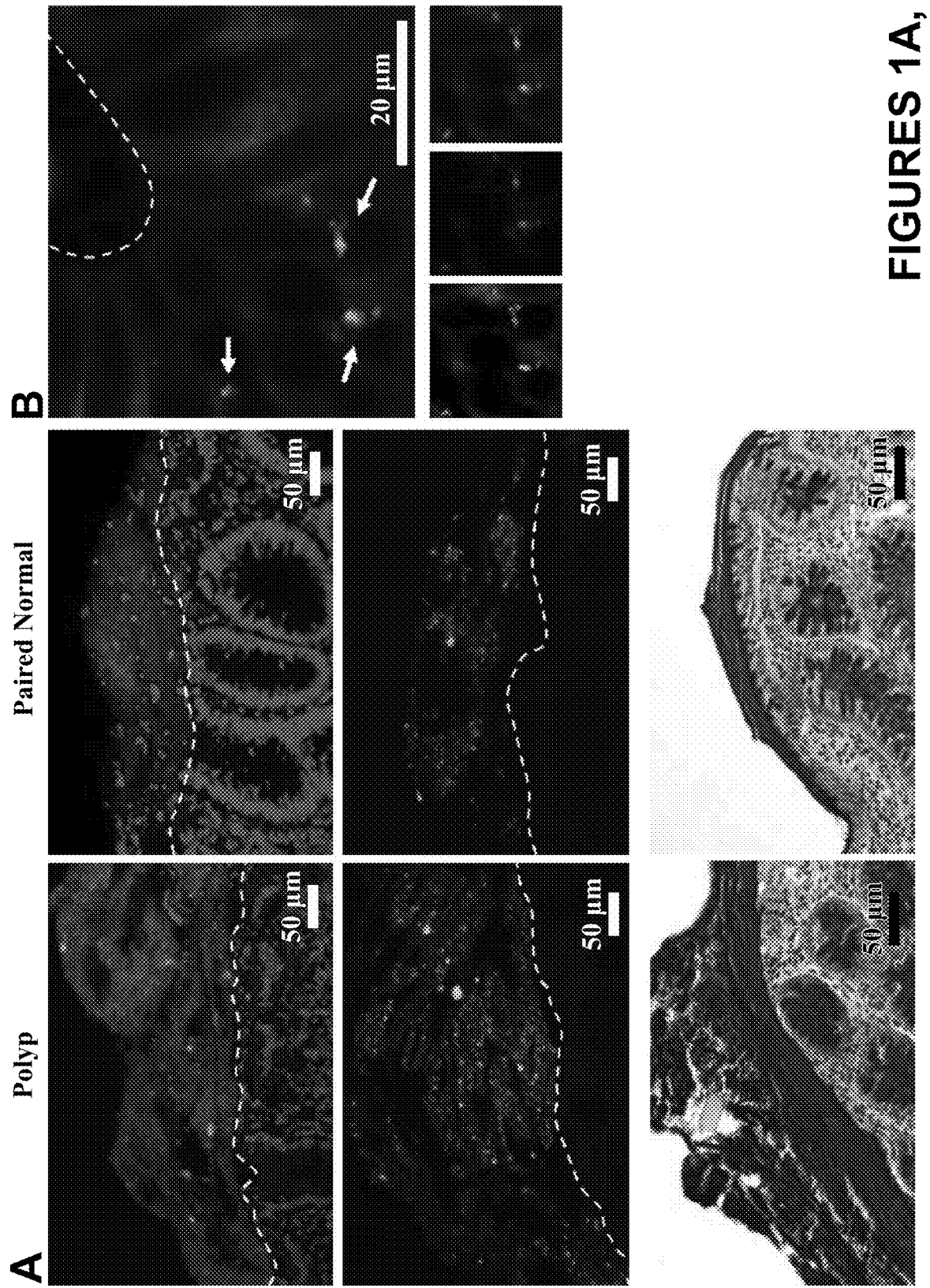
FIGS. 1A-1D depict fluorescent in situ hybridization (FISH) and microbiology culture analysis of FAP mucosal tissues.

Individuals with sporadic colorectal cancer (CRC) frequently harbor abnormalities in the composition of the gut microbiome; however, the microbiota associated with precancerous lesions in hereditary CRC remains largely unknown.

Accordingly, colonic mucosa of patients with familial adenomatous polyposis (FAP), who develop benign precursor lesions (polyps) early in life were studied. Patchy bacterial biofilms composed predominantly of Escherichia coli and Bacteroides fragilis were identified. Genes for colibactin (clbB) and Bacteroides fragilis toxin (bft), encoding secreted oncotoxins, were highly enriched in FAP patients' colonic mucosa compared to healthy individuals. Tumor-prone mice cocolonized with E. coli (expressing colibactin), and enterotoxigenic B. fragilis showed increased interleukin-17 (IL-17) in the colon and DNA damage in colonic epithelium with faster tumor onset and greater mortality, compared to mice with either bacterial strain alone. These data provide evidence for an unexpected link between early neoplasia of the colon and tumorigenic bacteria.

Treatment of Cancer

When healthy, the colon is covered by a mucus layer that segregates the microbiota from direct contact with the host colonic epithelium. Breaches of this protective mucus layer with resulting increased contact between mucosal microbiota and the colonic epithelial cells has been proposed as a critical first step in inciting changes in tissue biology and/or inflammation that yield chronic colonic disease such as inflammatory bowel disease. Concomitant with increased access to the mucosal epithelium, microbial community communication (such as quorum sensing) has been predicted to change, modifying bacterial structure and function and often resulting in biofilm formation. Biofilms have been defined as aggregations of microbial communities encased in a polymeric matrix that adhere to either biological or non-biological surfaces. Biofilms that invade the mucus layer and come into direct contact with mucosal epithelial cells have indicated pathology although limited detection of biofilms in otherwise histologically normal mucosa has been observed in the colon. Biofilms characterize numerous chronic mucosal disease states in and outside of the colon (including inflammatory bowel diseases, cystic fibrosis, pharyngo-tonsillitis, otitis media, rhinosinusitis, urethritis and vaginitis) where direct bacterial contact with epithelial cells results in perturbed epithelial function and chronic inflammation. However, no association of biofilms with CRC pathologic states has been reported.

Accordingly, in certain embodiments, a method for treating cancer, e.g. colorectal cancer (CRC) in a subject, comprises administering a therapeutically effective amount of one or more agents which are bactericidal, bacteriostatic and/or inhibit growth or activity of bacteria in a bacterial biofilm in the subject's gastrointestinal tract, wherein the bacterial biofilm comprises at least one bacterial type from *Bacteroides* and at least one bacterial type from Enterobacteriaceae.

In certain embodiments, the at least one bacterial type from *Bacteroides* is enterotoxigenic *Bacteroides fragilis* (ETBF) and the at least one bacterial type from Enterobacteriaceae is *Escherichia coli* (*E. coli*). In certain embodiments, the *E. coli* bacteria comprise polyketide synthase (pks) genes. In certain embodiments, the *E. coli* bacteria encode colibactin genotoxin and the enterotoxigenic *Bacteroides fragilis* (ETBF) encode a *Bacteroides fragilis* toxin. In certain embodiments, the ETBF and *E. coli* co-colonize the subject's gastrointestinal tract.

In certain embodiments, the method of treating a subject suffering from colorectal cancer includes administration of one or more chemotherapeutic agents.

In other embodiments, a method of preventing colorectal cancer or treating a subject for colorectal cancer, comprises administering to the subject an antimicrobial agent and/or probiotic, wherein colibactin (clbB) and *Bacteroides fragilis* toxin (bft), are detected in mucosa of a subject's gastrointestinal tract. In certain embodiments, the antibacterial agents inhibit: growth, activity or are bactericidal to enterotoxigenic *Bacteroides fragilis* (ETBF) and/or *Escherichia coli* (*E. coli*).

In other embodiments, a method of treating a neoplastic condition in a subject comprises (i) detecting a bacterial biofilm within the gastrointestinal tract of a subject; and (ii) administering an antimicrobial agent or a probiotic agent to the subject in an amount effective to reduce the size of the bacterial biofilm. In certain embodiments, the bacterial biofilm is detected within the colon of the subject and comprises enterotoxigenic *Bacteroides fragilis* (ETBF) and *Escherichia coli* (*E. coli*). In certain embodiments, the ETBF and/or *E. coli* are detected by one or more assays comprising in situ hybridization, blotting, polymerase chain reaction (PCR), immunoassays, reporter assays, or any combinations thereof. In some embodiments, the bacterial biofilm is positive for colibactin (clbB) and *Bacteroides fragilis* toxin (bft).

In certain embodiments, a method of treating colorectal cancer, comprises administering a chemotherapeutic agent and a pharmaceutical composition comprising a therapeutically effective amount of an antimicrobial agent to a subject in need thereof, wherein the antimicrobial agents comprise one or more bactericidal and/or bacteriostatic agents for enterotoxigenic *Bacteroides fragilis* (ETBF) and/or *Escherichia coli* (*E. coli*). In certain embodiments, the method further comprise administering a probiotic.

Compositions: In certain embodiments, compositions for preventing or treating colorectal cancer comprises a therapeutically effective amount of one or more antibacterial agents and/or one or more probiotics, wherein the antibacterial agents are bactericidal and/or bacteriostatic for enterotoxigenic *Bacteroides fragilis* (ETBF) and *Escherichia coli* (*E. coli*).

In certain embodiments, a pharmaceutical composition comprises a therapeutically effective amount of one or more bactericidal and/or bacteriostatic agents for enterotoxigenic *Bacteroides fragilis* (ETBF) and/or *Escherichia coli* (*E. coli*). In certain embodiments, the pharmaceutical composition comprises a probiotic agent, a chemotherapeutic agent or a combination thereof.

In certain embodiments, the antibacterial agents or agents are bactericidal, bacteriostatic and/or inhibit growth or activity of bacteria comprise antibacterial agents, probiotics, mucosal protective agents, vaccines, antibodies, mucosal antigen specific immune cell modulating agents, anti-inflammatory agents, anti-cytokine agents, cytokines, small molecule compounds, antisense oligonucleotides, antibiotics, species-specific bacteriophages, small molecule inhibitors, toxins, membrane destabilizing agents, antibacterial or antimicrobial compounds, siRNA reagents, antibodies, antibody fragments bearing epitope recognition sites, such as Fab, Fab', F(ab')$_2$ fragments, Fv fragments, single chain antibodies, antibody mimetics (such as DARPins, affibody molecules, affitins, affitins, anticalins, avimers, fynomers, Kunitz domain peptides and monobodies), peptoids, aptamers; cytokines, cellular factors, enzymes, immune cell modulating agents, adoptive cell therapeutics, peptides, organic or inorganic molecules, natural or synthetic compounds and the like, or combinations thereof. In certain embodiments, the antibacterial agents comprise one or more antibiotics comprising: clindamycin, beta-lactams, macrolides, chloramphenicol, aminoglycosides, fluoroquinolones, carbapenems, sulbactam or combinations thereof. Examples of beta lactams include, without limitation: carbenicillin, cefoperazone, cefamandole and penicillin. In certain embodiments, the mucosal antigen specific immune cell modulating agents comprise: B-cell activating factor (BAFF), cytokines, peptides, vectors expressing one or more peptides, or combinations thereof. The peptides comprise one or more antigenic epitopes of ETBF and/or *E. coli* inducing an antigen specific immune response. In certain embodiments, the anti-cytokine agent inhibits IL-17 induction by ETBF bacteria.

In certain embodiments, the at least one bacterial type from *Bacteroides* is enterotoxigenic *Bacteroides fragilis* (ETBF) and the at least one bacterial type from Enterobacteriaceae is *Escherichia coli* (*E. coli*). In certain embodiments, the *E. coli* bacteria comprise polyketide synthase (pks) genes. In certain embodiments, the *E. coli* bacteria encode colibactin genotoxin and the enterotoxigenic *Bacteroides fragilis* (ETBF) encode a *Bacteroides fragilis* toxin.

In certain embodiments, the ETBF and *E. coli* co-colonize the subject's gastrointestinal tract.

In certain embodiments, the antibacterial agent is bactericidal for ETBF and/or *E. coli*. In other embodiments, the antibacterial agents inhibits bacterial adherence to the subject's gastrointestinal tract.

In certain embodiments, the probiotic agent comprises one or more species of selected from the group consisting of *Bacteroides, Prevotella, Porphyromonas, Fusobacterium, Sutterella, Bilophila, Campylobacter, Wolinella,* Butyrovibrio, *Megamonas, Desulfomonas, Desulfovibrio, Bifidobacterium, Lactobacillus, Eubacterium, Actinomyces, Eggerthella, Coriobacterium, Propionibacterium,* non-spore-forming anaerobic gram-positive bacilli, *Bacillus, Peptostreptococcus Peptococcus, Acidaminococcus, Ruminococcus, Megasphaera,* Gaffkya, *Coprococcus, Veillonella, Sarcina, Clostridium, Aerococcus, Streptococcus, Enterococcus, Pediococcus, Micrococcus, Staphylococcus, Corynebacterium,* Enterobacteriaceae, Pseudomonadaceae or combinations thereof.

In certain embodiments, the composition comprises one or more chemotherapeutic agents. Examples of chemotherapeutic agents include Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozcicsin, carzcicsin and bizcicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylomithine (DMFO); retinoids such as retinoic acid; capecitabine; and pharmaceutically acceptable salts, acids or derivatives of any of the above.

Also included as chemotherapeutic agents are: (i) anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON™ toremifene; (ii) aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME™ ribozyme) and a HER2 expression inhibitor; (ix) vaccines such as gene therapy vaccines, for example, ALLOVEC- TIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

Currently available chemotherapies and their dosages, routes of administration and recommended usage are known in the art and have been described in such literature as the Physician's Desk Reference (60th ed., 2006). Routes of administration include parenterally, intravenously, subcutaneously, intracranially, intrahepatically, intranodally, intraureterally, subureterally, subcutaneously, and intraperitoneally.

In one embodiment, a therapeutically effective amount of an antibacterial or antimicrobial agent (e.g., antibiofilm agent) described herein for a method of treating cancer is an amount of sufficient to induce apoptosis of cancer cells of the subject as compared to in the absence of one or both such agents. In other embodiments, the amount(s) that is safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of an antimicrobial agent described herein can inhibit further tumor growth, cause a reduction in size or even completely halt tumor growth, shrink the sizes of tumor, even complete regression of tumor, and reduce clinical symptoms associated with tumor. In certain embodiments, an effective amount for treating cancer is an amount of an antimicrobial agent described herein sufficient to result in a reduction or complete removal of the symptoms of the disorder, disease, or medical condition. In some embodiments, an effective amount for treating or ameliorating a disorder, disease, or medical condition is an amount sufficient to result in a reduction or complete removal of the symptoms of the disorder, disease, or medical condition. In the case of tumor (e.g., a cancerous tumor), the therapeutically effective amount of the antimicrobial agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antimicrobial agent may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount". However, for any given case, an appropriate "effective amount" can be determined by a skilled artisan according to established methods in the art using only routine experimentation. In one embodiment, as used herein, the term "treat or treatment" refers to reducing or alleviating at least one adverse clinical symptom associated with cancer, e.g., pain, swelling, low blood count etc. In another embodiment, the term "treat' or treatment" refers to slowing or reversing the progression neoplastic uncontrolled cell multiplication, i.e. shrinking existing tumors and/or halting tumor growth. In another embodiment, the term "treat' or treatment" refers to inducing apoptosis in cancer or tumor cells in the subject.

Immune Modulating Agents and Mucosal Immunity: In certain embodiments, the compositions comprise one or more immune-modulating agents which are involved in activating and maintaining an antigen specific immune response. In certain embodiments, the agents activate and maintain antigen specific mucosal immunity.

The mucosal immune system (MIS) provides protection against toxic elements that enter the body through mucous membranes. The MIS comprises the largest immune organ in the human body. It can be viewed as a single layer epithelium covered by mucus and anti-microbial proteins that is reinforced by various aspects of innate and adaptive immunity (McGhee and Fujihashi 2012; Inside the Mucosal Immune System. *PLoS Biol* 10, e1001397).

In its simplest form, the MIS can be divided into inductive and effector sites based on their anatomical and functional properties. The mucosal inductive sites are collectively called mucosa-associated lymphoid tissue (MALT) and include gut-associated lymphoid tissues (GALT), nasopharyngeal-associated lymphoid tissue (NALT) and lymphoid sites. The MALT provides a continuous source of memory B and T cells that then move into effector sites. Mucosal effector sites include the lamina propia regions of the gastrointestinal, upper respiratory and reproductive tracts as well as secretory glandular tissues. These sites contain antigen-specific mucosal effector cells such as IgA-producing plasma cells, and memory B and T cells.

Proinflammatory cytokines such as tumor necrosis factor (TNF), IFN-γ, and IL-13, are upregulated in the inflamed mucosa. Other agents include: growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and IL-12 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be used and administered.

CD4$^+$ T cells acquire distinct functional properties in response to signals conveyed by commensal and pathogenic microbe-activated cells of the innate immune system. T-helper type 1 ($T_H1$) and $T_H2$ cells control intracellular microorganisms and helminths, respectively, whereas the induced regulatory T cells (iTreg) suppress excessive immune responses. $T_H17$ cells secrete IL-17, IL-17F, and IL-22, and have significant roles in protecting the host from bacterial and fungal infections, particularly at mucosal surfaces. $T_H17$ cells are most abundant at steady state in gut-associated tissues, particularly the small intestinal lamina propria (SI LP), where they accumulate only in the presence of luminal commensal microbiota.

B-cells also play an important role in the humoral as well as cellular immune response. Immature B-cells originate in bone marrow and migrate to spleen, where they become transitional B-cells, whereas some of them further differentiate into mature B-cells. Generally, the presence of the B-cell activating factor (BAFF) is of essential importance for normal development of B-cells.

B-cell activating factor (BAFF, also called BLyS, Tall-1, or TNFSF13), a member of the TNF (tumor necrosis factor) family, is an important cytokine that controls B-cell survival and maturation. BAFF triggers the production of specific subclasses of antibodies in the B-cells, such as IgG, IgA, and IgE, and is also involved in the immunological class-switching reactions. It seems that the aberrant signaling in the pathways that require BAFF is closely related to numerous diseases, e.g. allergies, autoimmune diseases, infections as well as some cancer diseases, in which dysregulation occurs both at the level of humoral and cellular immunity (Cerutti A, Puga I, Cols M: Innate control of B cell responses. *Trends Immunol.* 2011 May; 32(5):202-11; Lied G A, Berstad A.: 48. Functional and clinical aspects of the B-cell-activating factor (BAFF): a narrative review. *Scand J Immunol.* 2011 January; 73(1):1-7.; Cancro M P: The BLyS family of ligands and receptors: an archetype for niche-specific homeostatic regulation. *Immunol Rev.* 2004 December; 202:237-49). BAFF is an important factor in numerous immunostimulatory reactions (Tertilt C, J et al. *Infect Immun.* 2009 July; 77(7):3044-55).

Accordingly, in certain embodiments, a method of treating colorectal cancer comprises administering to a subject in need of such treatment, a pharmaceutical composition comprising a therapeutically effective amount of one or more antimicrobial agents for enterotoxigenic *Bacteroides fragilis* (ETBF) and/or *Escherichia coli* (*E. coli*) and one or immune activating agents to induce an antigen specific immune response. In certain embodiments, the immune activating agents induce a mucosal immune response. In certain embodiments, the subject is further treated with a probiotic agent, a chemotherapeutic agent or a combination thereof. In certain embodiments, an anti-cytokine agent inhibits IL-17 induction by ETBF bacteria.

In certain embodiments, a subject is administered a vaccine expressing or comprising immunogenic peptides wherein the peptides comprise one or more epitopes of ETBF and/or *E. coli* for inducing an antigen specific immune response.

Probiotics: A therapy that can be administered alone or in conjunction with one or more of the therapies discussed herein, is probiotic therapy. "Probiotic" therapy is intended to mean the administration of organisms and substances which help to improve the environment of the intestinal tract by inhibiting the disproportional growth of bacteria which produce toxins in the intestinal tract. For example, in healthy humans, the small intestine is colonized by lactobacilli (e.g., *L. acidophilus*), *Bifidobacterium*, gram-negative anaerobes, enterococci, and Enterobacteriaceae; the large intestine is colonized mainly by obligate or facultative anaerobes (e.g., *Bacteroides* sp., gram-positive anaerobic cocci, *Clostridium* sp., non-spore forming gram-positive rods, Enterobacteriaceae (mainly *E. coli*), and enterococci). Some of these bacteria produce substances which suppress harmful bacteria; for example, bifidobacteria produce lactic and acetic acid, decreasing the pH of the intestines. They can also activate macrophages, which also help suppress harmful bacteria.

Probiotic agents comprise one or more of the following normal inhabitants of the human intestinal tract: any species of *Bacteroides, Prevotella, Porphyromonas, Fusobacterium, Sutterella, Bilophila, Campylobacter, Wolinella,* Butyrovibrio, *Megamonas, Desulfomonas, Desulfovibrio, Bifidobacterium, Lactobacillus, Eubacterium, Actinomyces, Eggerthella, Coriobacterium, Propionibacterium,* other genera of non-sporeforming anaeroibic gram-positive bacilli, *Bacillus, Peptostreptococcus* (and newly created genera originally in *Peptostreptococcus*), *Peptococcus, Acidaminococcus, Ruminococcus, Megasphaera,* Gaffkya, *Coprococcus, Veillonella, Sarcina,* certain of the species of *Clostridium, Aerococcus, Streptococcus, Enterococcus, Pediococcus, Micrococcus, Staphylococcus, Corynebacterium,* and species of the genera comprising the Enterobacteriaceae and Pseudomonadaceae, as well as mixtures thereof.

Certain strains for supplementation are those that are typically permanent residents of the human intestinal tract and which do not produce toxins. Normal human intestinal flora are better adapted to the environment (bile acids, anaerobic conditions, etc.) of the human intestinal tract, and are more likely to survive and colonize the human intestinal tract. Certain species such as *L. bulgaricus* and *S. thermophilus*, for example, are commonly used as probiotics, but are not normal constituents of human gut flora, and such species apparently do not colonize the intestinal tract well.

A probiotic therapy can be designed to be administered as a mixture of a large number of species that are normal, benign inhabitants of the gut, optionally in the general proportion in which they are found in healthy humans. For example, *E. coli* is—a common enteric inhabitant, but makes up only about 1/1000 of the bowel flora found in healthy humans, so would be a relatively small proportion of a probiotic mixture. Alternatively, the probiotic can be designed in different proportions to facilitate displacement of harmful bacteria or to prevent further adherence to the gut mucosa of harmful bacteria.

Certain probiotic diet items have also been described, e.g., fermented vegetables (sauerkraut, kimchi, collars, kale, celery), yogurt drinks, tempeh, natto and fermented raw milk (e.g., kefir, yogurt).

Delivery Agents: Delivery vehicles as used herein, include any types of molecules for delivery of the compositions embodied herein, both for in vitro or in vivo delivery. Examples, include, without limitation: nanoparticles, colloidal compositions, lipids, liposomes, nanosomes, carbohydrates, organic or inorganic compositions and the like. In certain embodiments, the delivery vehicles comprise vaccines, peptides, adjuvants, immune-modulating agents, which can be administered with the antibacterial agents embodied herein.

The compositions of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-lam in diameter can be used. The polynucleotide is encapsulated in these microparticles, which are taken up by macrophages and gradually biodegraded within the cell, thereby releasing the composition(s). A second type of microparticle is intended not to be taken up directly by cells, but rather to serve primarily as a slow-release reservoir of the composition(s) that is taken up by cells only upon release from the micro-particle through biodegradation. These polymeric particles should therefore be large enough to preclude phagocytosis (i.e., larger than 5 μm and preferably larger than 20 μm). Another way to achieve uptake of the composition(s) is using liposomes, prepared by standard methods. The composition(s) can be incorporated alone into these delivery vehicles or co-incorporated with tissue-specific antibodies, for example antibodies that target cell types that are commonly infected.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol modified (PEGylated) low molecular weight LPEI.

Pharmaceutical Compositions

In certain embodiments, the present invention provides for a pharmaceutical composition comprising an antimicrobial agent or probiotic agent of the present invention. The antimicrobial agent or probiotic agent can be suitably formulated and introduced into a subject or the environment of the cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of an antibiotic agent and/or a probiotic agent for preventing formation and/or reducing the size of a biofilm in a subject (i.e., an effective dosage) depends upon the antibiotic agent and/or probiotic agent selected. For instance, single dose amounts of an antibiotic agent in the range of approximately 1 pg to 1000 mg may be administered; in some embodiments, 10 pg, 30 pg, 100 pg, or 1000 pg, or 10 ng, 30 ng, 100 ng, or 1000 ng, or 10 µg, 30 µg, 100 µg, or 1000 µg, or 10 mg, 30 mg, 100 mg, or 1000 mg may be administered. In some embodiments, 1-5 g of the compositions can be administered. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an antibiotic agent and/or a probiotic agent can include a single treatment or, preferably, can include a series of treatments.

Suitable amounts of an antibiotic agent and/or a probiotic agent must be introduced and these amounts can be empirically determined using standard methods. Exemplary effective concentrations of individual antibiotic agents and/or probiotic agents in the gut of a subject can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

Dosage

Dosage of one or more antibiotic, probiotic, or, optionally, other cancer therapy agents of the invention can be determined by one of skill in the art and can also be adjusted by the individual physician in the event of any complication. Typically, the dosage ranges from 0.001 mg/kg body weight to 5 g kg body weight. In some embodiments, the dosage range is from 0.001 mg/kg body weight to 1 g kg body weight, from 0.001 mg kg body weight to 0.5 g/kg body weight, from 0.001 mg/kg body weight to 011 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight. Alternatively, the dose range will be titrated to maintain serum levels between 5 g/mL and 30 g/mL.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose.

Efficacy testing can be performed during the course of treatment using the methods described herein, e.g., ultrasound, MRI and CT to monitor the shrinkage in size of the tumors in the treated subject. A decrease in size of the tumors during and after treatment indicates that the treatment is effective in reducing tumor size. Measurements of the degree of severity of a number of symptoms associated with cancerous tumors are also noted prior to the start of a treatment and then at later specific time period after the start of the treatment. A skilled physician will be able to ascertain the tumor sizes and related symptoms by known methods in the art and those described herein.

Combination Therapies

In a specific embodiment, cycling therapy involves the administration of a first cancer therapeutic for a period of time, followed by the administration of a second cancer therapeutic for a period of time, optionally, optionally followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). When two prophylactically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In another embodiment, a first prophylactically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention.

EXAMPLES

Example 1: Patients with Familial Adenomatous Polyposis Harbor Colonic Biofilms Containing Tumorigenic Bacteria Biofilms on normal mucosa of sporadic CRC patients are associated with a pro-oncogenic state (6, 7), suggesting that biofilm formation is an epithelial event influencing CRC. To test the hypothesis that biofilm formation may be an early event in the progression of hereditary colon cancer, the mucosa of FAP patients were examined at clinically indicated colectomy.

Materials and Methods

Patient Selection and Sample Acquisition: Polyps and paired normal tissues were collected from patients with a clinical FAP phenotype undergoing colon surgery at Johns Hopkins Hospital. A subset of patients underwent genetic counseling and mutational analysis confirming a mutation in the APC gene (Table 1). Control subjects (colonoscopy and surgical) included individuals without a history of CRC, inflammatory bowel disease, or antibiotic usage within three months (Table 2, FIG. 1C). Grossly normal colon mucosal biopsies (colonoscopy, samples S55-S71, Table 2) and colon tissue from surgical resections (3714, 3723, 3724, 3730, 3734, 3737, Table 2) not needed for pathologic diagnosis were collected. Normal colon tissue from an additional subject 3760, a patient with CRC, was used as a bft-negative control in FIG. 1D. Bowel preparations prior to surgery or colonoscopy were determined by the attending surgeon or gastroenterologist. Two bowel preparations were typically used (mechanical bowel preparation [MIRALAX™], or Fleet PHOSPHO-SODA™ enema). All colonoscopy patients received a bowel preparation whereas some surgical patients, both FAP and non-FAP patients, received no bowel preparation prior to surgery. Previous data suggested no relationship between bowel preparation and biofilm detection (6). Pre-operative intravenous antibiotics were administered in all surgical cases (cefotetan or clindamycin/gentamycin) immediately preceding surgery. One patient received oral antibiotics on the night prior to surgery as noted in the patient metadata (Table 1). Biopsies and tissues were rapidly preserved in Carnoy's solution, RNAlater, anaerobic transport media or snap frozen for subsequent analysis. This study was approved by the Johns Hopkins Institutional Review Board. All samples were obtained in accordance with the Health Insurance Portability and Accountability Act (HIPAA).

Fluorescent in situ hybridization: Carnoy's fixed, paraffin-embedded tissues were sectioned to 5 μm thickness and de-waxed following standard procedures. Sections were stained with Periodic acid Schiff (PAS) to confirm mucus presence and preservation and successive sections were hybridized with the Eub338 universal bacterial probe (Table 4). Slides were imaged using a Nikon E800 microscope with NIS elements software. Samples that were determined to have a bacterial presence by universal probe were next analyzed by the more specific probe set listed in Table 4

(Life Technologies). Probes were applied to slides at a concentration of 2 pmol/µl in prewarmed hybridization buffer (900 mM NaCl, 20 mM Tris pH 7.5, 0.01% SDS, 20% formamide). Slides were incubated at 46° C. in a humid chamber for 2 hours, and washed at 48° C. for 15 minutes in wash buffer (215 mM NaCl, 20 mM Tris pH 7.5, 5 mM EDTA). Slides were mounted using ProLongGold antifade reagent (Life Technologies).

Biofilm quantification: As previously published (6), bacterial biofilms were defined as invasive bacterial aggregates within the colon mucus with a bacterial density >$10^9$ bacteria/mL. Bacterial biofilms were quantified for longitudinal distance along the epithelium and density using slides hybridized with the universal bacterial probe (Table 4). When possible, up to five biofilm measurements were taken across the length of the histologic section (some samples did not have five patches of biofilm, in these cases all present biofilms were measured). Relative biofilm species quantification was performed using tissues hybridized with the universal bacterial probe along with group and *B. fragilis* and *E. coli* species specific probes (Tables 3 and 4). Because tissue sections were similar qualitatively within an individual patient, one tissue section per patient was selected for *E. coli* and *B. fragilis* quantification. For quantification, images were taken at 100× magnification and individual bacterial cells (all bacteria, *E. coli*, and *B. fragilis*) in a 10×10 µm space were counted. Five 10×10 µm boxes on a single tissue section were counted per patient to determine the relative biofilm composition as a percentage.

Microbial Culture

Detection of pks+ *E. coli* and ETBF by culture: Tissue stored at −80° C. was utilized for microbial culture and selective amplification and identification of *E. coli* and *B. fragilis* isolates. Two to four mucosal samples per patient were available for microbiology culture analysis (Tables 1 and 2). An approximately 3 mm diameter punch of mucosal samples from surgically-resected control tissue, FAP polyp, FAP paired normal, or colonoscopy biopsy was placed in tryptic soy broth (TSB) or peptone yeast glucose bile broth (PYGB) and grown in aerobic or anaerobic conditions, respectively, at 37° C. for up to 48 hours. Microbial growth was pelleted and an aliquot preserved at −80° C. for PCR detection of clbB and *E. coli* (TSB culture) and bft and *B. fragilis* (PYGB culture). The remaining pellet was diluted and plated on semi-selective agar (aerobic TSB culture plated on MacConkey agar and anaerobic PYGB culture plated on BBE agar) for single colony identification. A total of fifty Lac$^+$ or bile-esculin$^+$ colonies was selected for PCR from each sample. PCR detection was performed using clbB primers (163 bp product) or bft primers (281 bp product) (Table 6).

Figure 8:
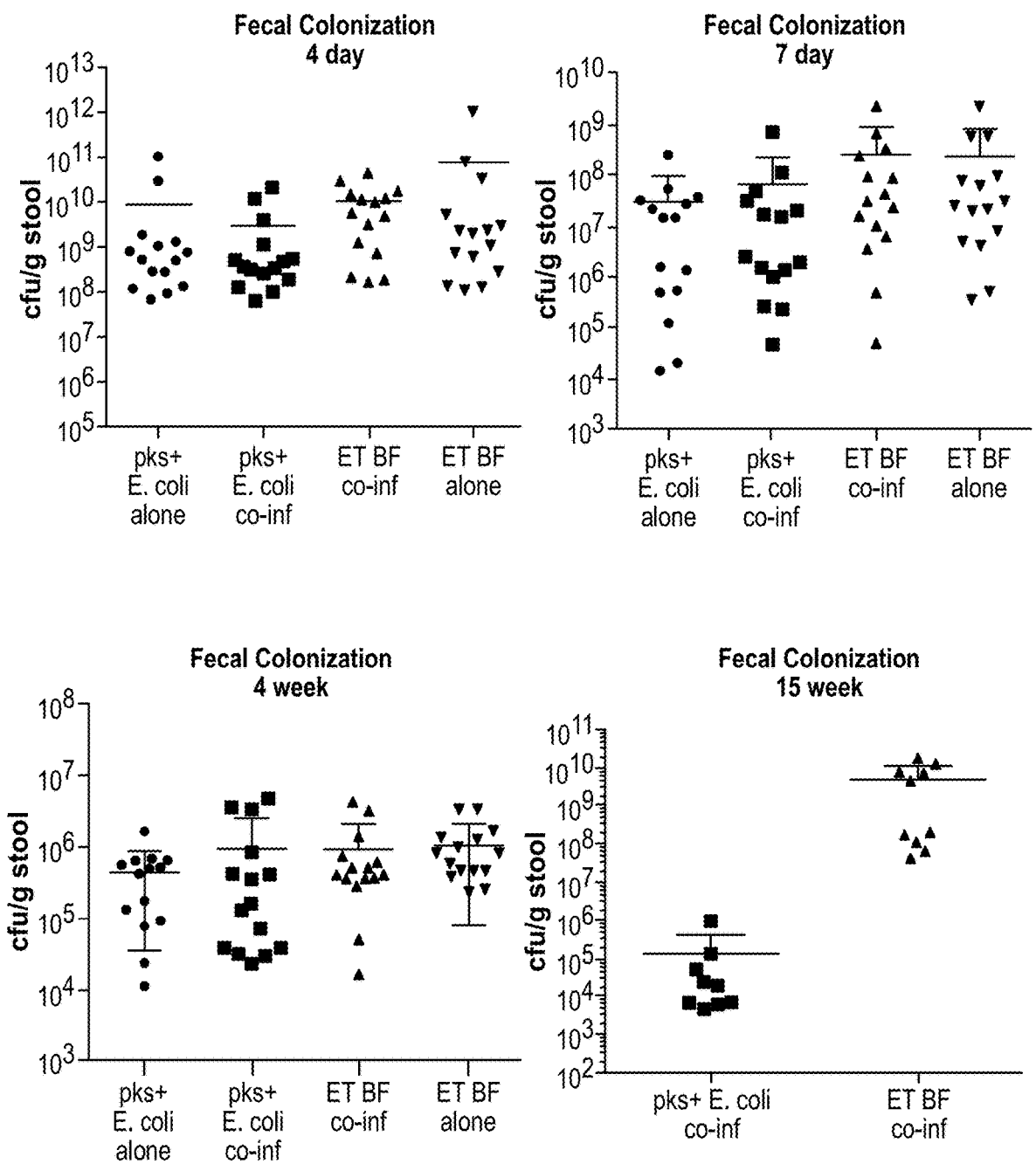
FIG. 8 shows the fecal colonization over time of ETBF and pks+ E. coli in mono-colonized and co-colonized AOM mouse model. Fecal colonization was present among all colonization conditions over time in the AOM mouse model. Fecal colonization is plotted as mean+/−SEM of colony-forming units (cfu) per gram of stool collected from mono-colonized (with pks+ E. coli or ETBF) or co-colonized (with pks+ E. coli/ETBF) mice at 4 days, 7 days and 4 weeks after bacterial inoculation. At 15 weeks culture data shown for co-colonization condition only. At 15 weeks, colonization for mono-colonized mice (pks+ E. coli or ETBF) was determined by qPCR yielding 7.6-8.7×10$^6$ cfu/gm for pks+ E. coli or 7.8-9.1×10$^6$ cfu/gm for ETBF. Data represent 3 independent experiments.
Figure 14A:
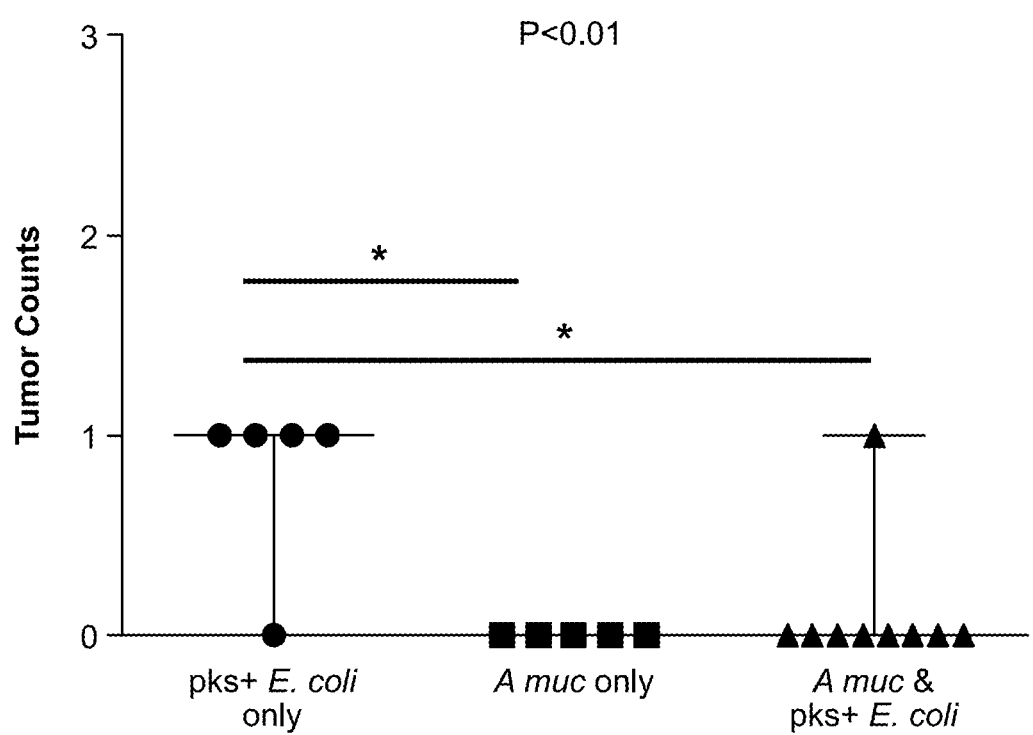
FIGS. 14A and 14B: AOM-treated mice co-colonized with pks+ E. coli and A. muciniphila (A muc) for 15 weeks do not display increased colon tumorigenesis.
Figure 14B:
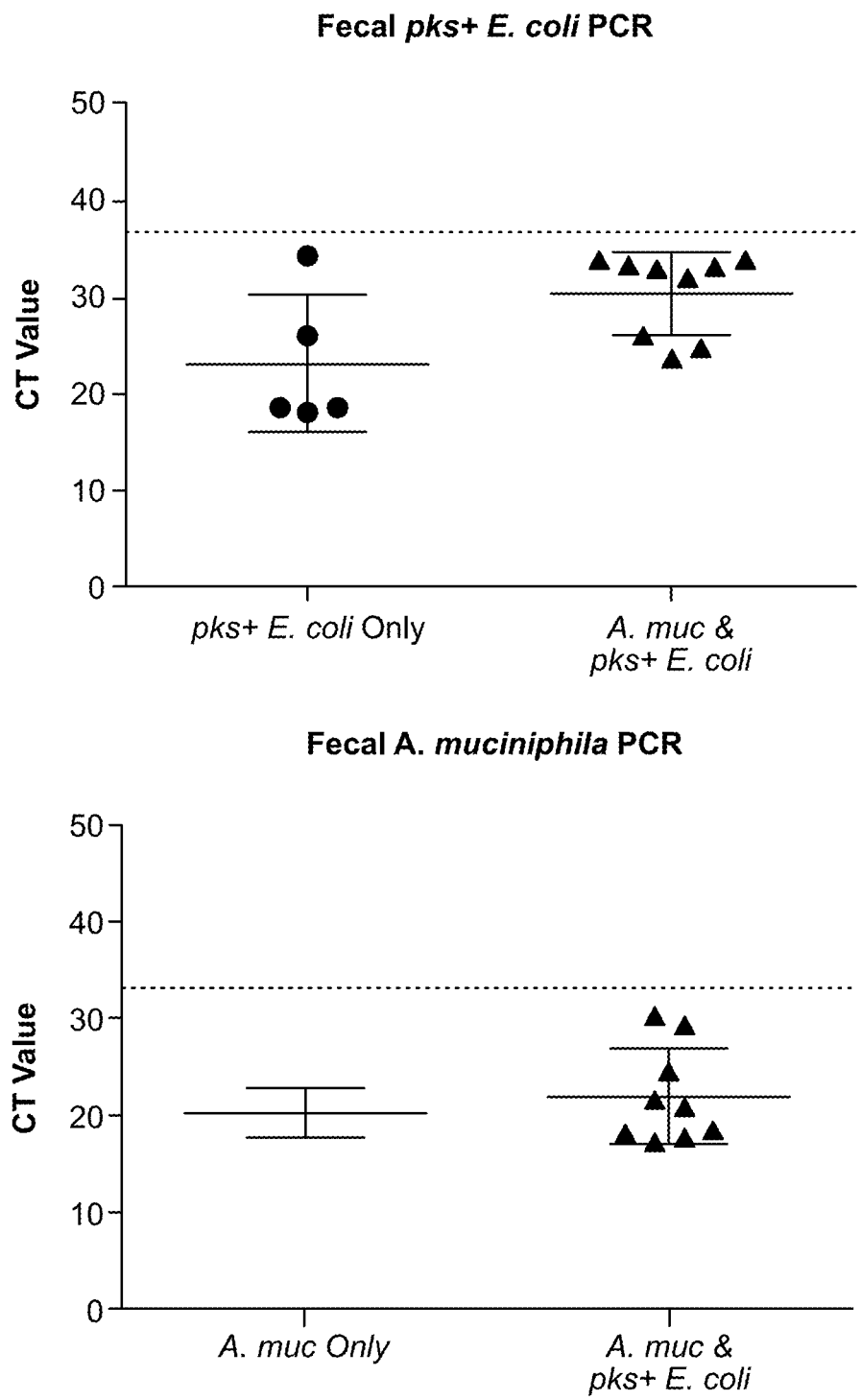

Bacterial Strains and Mouse Experiments: Two mouse colon tumorigenesis models were utilized: Apc$^{+/\Delta716}$ heterozygous multiple intestinal neoplasia (Min) mice (9) and specific pathogen free (SPF) C57BL/6J mice treated with AOM (10 mg/kg weekly for 6 weeks). In shorter experiments (<6 weeks) using the AOM model, AOM was given weekly until the time of mouse harvest. Prior to inoculation of bacterial strains in either mouse model, 6-week-old mice were given water containing 500 mg/L cefoxitin for 48 hours. Cefoxitin treatment results in an absence of detectable bacteria by culture or 16S rRNA qPCR by 24 hours (15). After removal of antibiotic water for 24 hrs, mice were inoculated by oral gavage with $10^8$ colony-forming units (cfu) ETBF (piglet 86-5443-2-2), $10^8$ cfu pks+ *E. coli* (murine NC101, expressing a fluorescent ampicillin resistance plasmid sfGFP-pBAD) or a mixture containing $10^8$ cfu of each strain. *Akkermansia muciniphila* was obtained from ATCC (ATCC® BAA-835™). ETBF was grown as previously described (9); pks+ *E. coli* was grown overnight in LB broth in a shaking incubator; and *A. muciniphila* was grown anaerobically overnight in brain heart infusion broth. Colonization was confirmed and quantified by collection and cultivation of stool on selective media for NC101::sfGFP and ETBF (MacConkey plates with ampicillin or BHI plates with 10 µg/ml clindamycin and 200 µg/ml gentamicin, respectively) (FIG. 8). For FIG. 14, colonization by NC101::sfGFP and *A. muciniphila* was assessed using stool DNA extracted from endpoint stools using Zymo Quick-DNA™ Fecal/Soil Microbe kit (Zymo Research), qPCR using 16S rRNA gene primer sets (Table 6) to detect pks+ *E. coli* and *A. muciniphila* quantitated as copy numbers per 100 ng stool DNA.

Mucosal colonization was confirmed and quantified on approximately 200 µg of tissue collected from the terminal 2 cm of the distal mouse colon. Tissue samples were washed by placing the tissue in 500 µl of 0.016% DTT saline followed by 30 sec vortex (speed 7-8), pelleting the tissue and discarding the DTT saline. After two washes, the tissue was homogenized and plated on selective media as described previously (13). Additional experiments were conducted with strains ETBF:Δbft (15) and NC101::Δpks (10). Mice were sacrificed at specified time-points, unless otherwise noted for poor health and/or excessive weight loss (defined as ≥20% total body weight). Germ-free C57BL/6 mice were similarly inoculated with ETBF or pks+ *E. coli* (mono-colonization) or a mixture of ETBF/pks+ *E. coli* (co-colonization) and harvested at ~48-60 hours after inoculation. Preliminary experiments determined that mono-colonized or co-colonized germ-free mice expired by ~72 hrs after bacterial inoculation.

Lamina propria lymphocyte isolation: Mouse colon was removed, flushed, and tissue was minced before enzymatic digestion with 400 U/ml liberase and 0.1 mg/ml DNAseI (Roche Diagnostics). Lymphocytes were isolated by percoll gradient separation (GE Healthcare life Science).

Figure 15A:
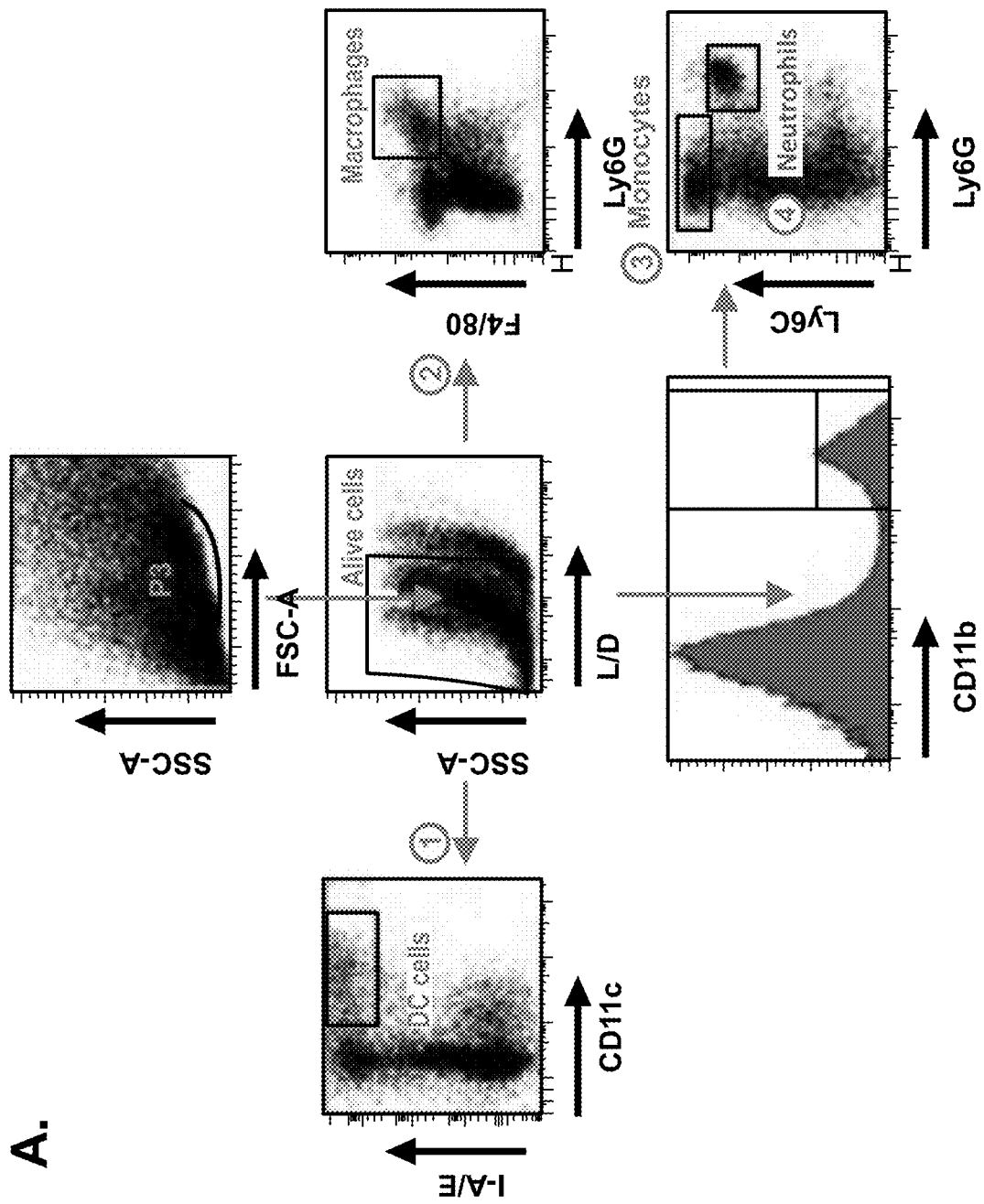
FIGS. 15A-15C show the flow cytometry gating strategy to delineate lymphoid, myeloid and IL-17-producing lamina propria lymphocytes.
Figure 15B:
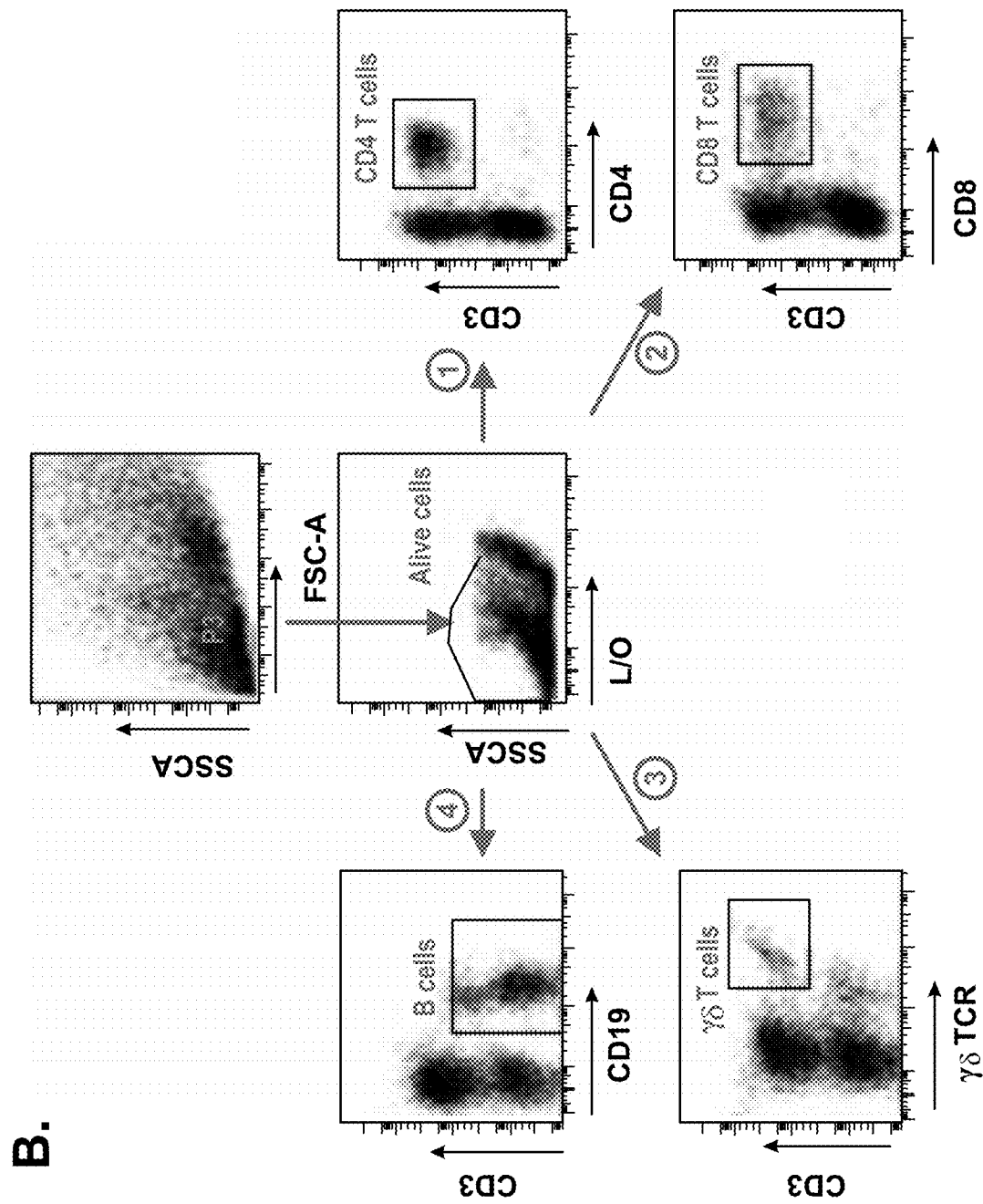
Figure 15C:
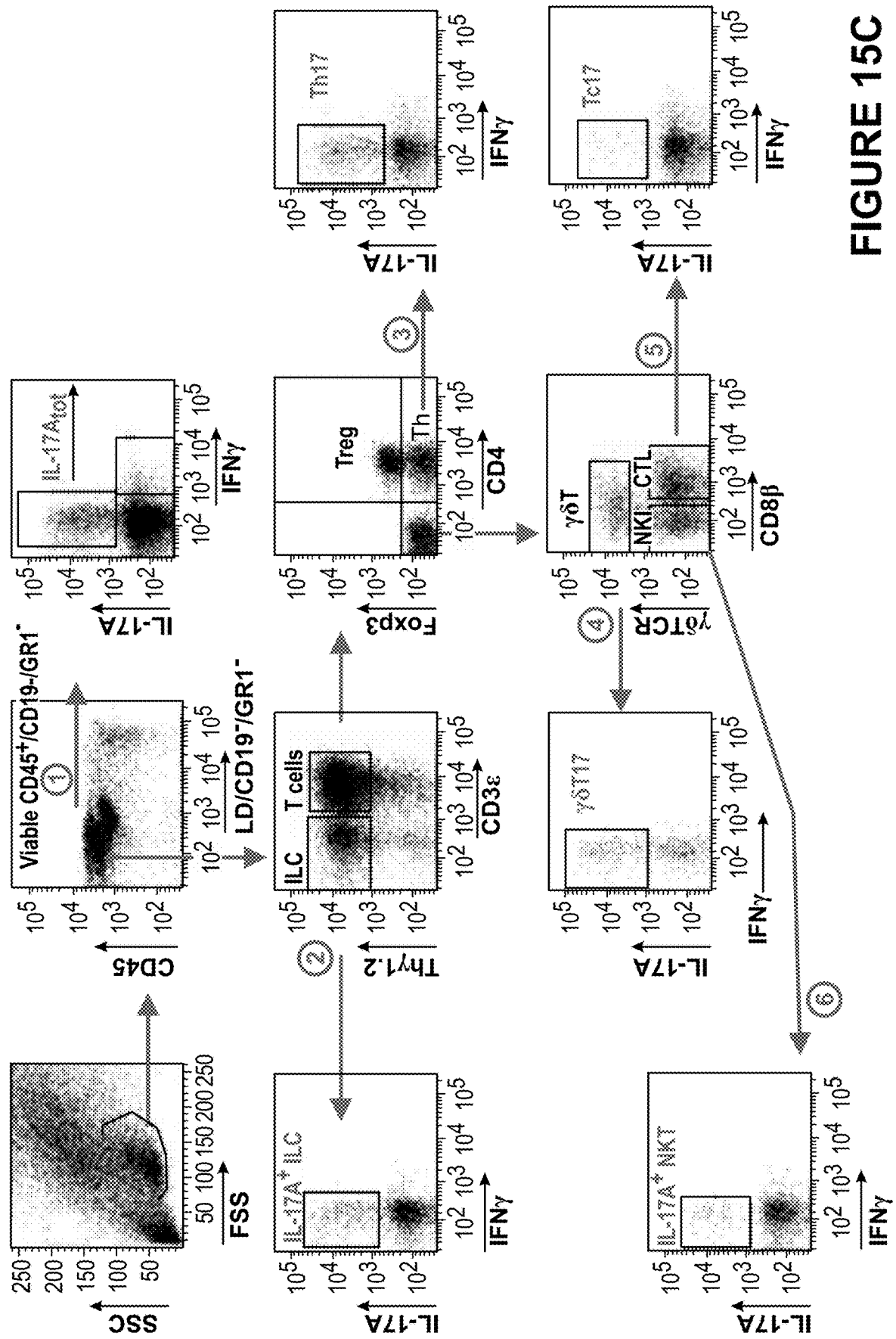

Flow cytometry: For surface marker staining, 1-2×$10^6$ cells were stained in 1 mL of 1× PBS with the LIVE/DEAD Fixable Aqua viability kit according to manufacturer's instructions (ThermoFisher Scientific), washed in an additional 2 mL of 1× PBS by centrifugation at 1500 rpm for 3 min, and then resuspended in 100 µL of 1× PBS containing 2% fetal calf serum and 1 µg of MOUSE FC BLOCK™ (BD Biosciences) for 10 minutes prior to the addition of the following fluorochrome-conjugated anti-mouse antibodies at the manufacturers' recommended concentrations for 30 min on ice: CD11b-PerCP/Cy5.5 (Clone M1/70, Biolegend), CD11c-APC (Clone N418, Miltenyi Biotec), MHC II (I-A/I-E)-APC/Cy7 (Clone M5/114.15.2, Biolegend), Ly6C-BV421 (Clone HK1.4, Biolegend), CD64-PE/Cy7 (Clone X54-5/7.1, Biolegend), F4/80-BV650 (Clone BM8, Biolegend), Ly6G-AF700 (Clone 1A8, Biolegend) or CD3-PerCP/Cy5.5 (Clone 145-2C11, eBioscience), CD4-BV605 (Clone RM4-5, Biolegend), CD8-PE (Clone 53-6.7, Biolegend), γδTCR-APC (Clone eBioGL3, eBioscience) and CD19-BV421 (Clone 6D5, Biolegend),. Stained cells were washed in 2 mL of 1× PBS containing 2% fetal calf serum by centrifugation at 1500 rpm for 3 min prior to resuspension in buffer and acquisition on a flow cytometer. Flow cytometry analysis of IL-17-producing cells (FIG. 3E) was performed using intracellular cytokine staining (ICS), following 3.5 hour in vitro stimulation of LP leukocytes (LPL) in presence of eBioscience stimulation plus protein transport inhibitor cocktail (PMA/Ionomycin/BrefeldinA/Monensin;

Thermofisher) as previously described (9). A BD LSR II instrument equipped with FACSDiva software (BD Biosciences) was used for data acquisition and FlowJo software (Tree Star Inc.) was utilized for analysis. Instrument compensation was performed prior to data acquisition using anti-rat/hamster or anti-mouse BDCOMPBEADS™ (BD Biosciences) according to the manufacturer's recommendations. Positive staining of live cells was determined against fluorescence-minus-one (FMO) controls after first gating away from debris, doublets, and dead cells. Conventional dendritic cells were defined as $CD11c^{Hi}/MHC\ II^{Hi}$ macrophages as CD64+/F4/80+, inflammatory monocytes as $CD11^{Hi}/Ly6C^{Hi}$, neutrophils as $CD11b^{Hi}/Ly6G^{Hi}$, CD4 T cells as $CD3^+/CD4^-$, CD8 T cells as $CD3^+/CD8^+$, γδ T cells as $CD3^+/\gamma\delta TCR^+$, and B cells as $CD3^-/CD19^+$ cells. The gating strategies are detailed in FIGS. 15A-15C.

Quantitative real-time PCR (IL-17a):An approximately 200 mg segment of distal mouse colon was processed for RNA isolation immediately following colon removal. Tissue was homogenized by bead beating in buffer ALS (Qiagen) and then run through a tissuelyzer column (Qiagen). The resultant solution was utilized for RNA extraction with RNeasy kit according to the manufacturer's recommended procedures. Transcription to complementary DNA was carried out using superscript III (Invitrogen). All qPCRs were performed in triplicate with TAQMAN primer/probe for IL-17a and 18s (as reference gene)(Applied Biosystems), and TAQMAN 2×mastermix (Applied Biosystems). The level of target mRNA was determined by the delta delta CT method.

ELISA for Fecal IgA: Nunc maxisorp plates were coated with 50 μg/μl Collagen I, Rat tail (Gibco) in 0.2 acetic acid overnight on a shaker at 4° C. Plates were subsequently washed twice with PBS before adding $10^9$ bacteria/ml in PBS (bacterial cultures were grown overnight and rinsed three times in PBS). Plates were incubated overnight at 37° C. in aerobic or anaerobic conditions (for NC101 and ETBF respectively). After incubation, plates were rinsed three times with PBS and fixed in 4% paraformaldehyde. Fixative was removed and plates were rinsed three times with PBS before blocking with 5% milk in PBS 0.05% tween 20 (PBST) for 1 hour at room temperature on a shaker. Fecal supernatants were prepared from 4 week stool samples resuspended at a concentration of 1 g/ml and centrifuged at 50 g for 10 minutes. Fecal supernatant was applied at 1:100 dilution in 2% milk PBST for 2 hours at room temperature on a shaker. Plates were rinsed three times in PBS followed by application of HRP-Goat Anti-mouse IgA (Life Technologies) at 1:1000 in 2% milk PBST for 1 hour at room temperature. Plates were rinsed three times in PBS and developed with TMB substrate (KPL).

Cell culture and mucus digestion assay: HT29-MTX-E12 cells were grown on transwell inserts (12 mm diameter, pore size 0.4 μm-Costar) in Dulbecco's modified Eagles Medium (DMEM) supplemented with 10% FCS at a density of $7.5×10^4$ cells per insert for 21 days. After confluence, the cells were treated with 10 μm DAPT (Sigma Aldrich) in the basolateral compartment for 6 days to stimulate mucus production, the apical compartment contained DMEM only. The media were refreshed every 2-3 days. After 21 days, tight junction formation was confirmed with trans-epithelial resistance measurements (TEER).

For mucus assays ETBF was grown in BHI (supplemented with hemin, vitamin K and L-cysteine) in an anaerobic jar for 24-48 hours until an OD of ~1.0 (9). Akkermansia mucinophila was grown in BHI with $N_2$ overlayed gas while shaking at 37° C. for 48 hours until ~OD 1.0. Escherichia coli NC101-GFP was grown in BHI overnight while shaking at 37° C. until ~OD 1.0. Next, bacteria were pelleted and resuspended at OD 0.2 in DMEM supplemented with 1% FCS and 10% BHI. Sterile DMEM with 1% FCS was added to the basolateral compartment and resuspended bacteria or medium control (DMEM with 1% FCS and 10% BHI) was added to the apical compartment at time 0 h. At 24 hours, cells were washed in warm PBS twice, fixed in Carnoy's solution for 10 minutes, dehydrated in 100% ethanol and cleared with xylene for 10 minutes. Next, liquid paraffin (58° C.) was added to the bottom and top of the transwell insert. Paraffinized membranes were embedded in the right orientation for sectioning at 5 μm. Sections were stained with alcian blue for mucus visualization.

Mucus depth was quantified in each condition in 5 random fields (40× magnification) of 100 μm length by measuring mucus depth every 10 μm on a VISIONTEK® (Sakura). Median mucus depth for each condition was calculated.

Immunohistochemistry: Formalin-fixed (10%), paraffin-embedded tissues were sectioned (5 μm) and stained. Slides were de-paraffinized and rehydrated following standard procedures. Slides were steamed in citrate buffer pH 6.0 for 45 minutes for antigen retrieval, and allowed to cool to room temperature, followed by blocking of endogenous peroxidase activity for 10 minutes with 3% hydrogen peroxide. Slides were blocked for 30 minutes in 10% normal goat serum, followed by primary antibody application overnight (1/500 rabbit anti-γH2AX [Bethyl Laboratories, IHC00008]). Slides were incubated with HRP-conjugated anti-rabbit IgG (Leica Biosystems, PV6119) for 30 minutes followed by DAB chromogen development for 10 minutes. All sections were counterstained with hematoxylin prior to mounting.

Figure 4A:
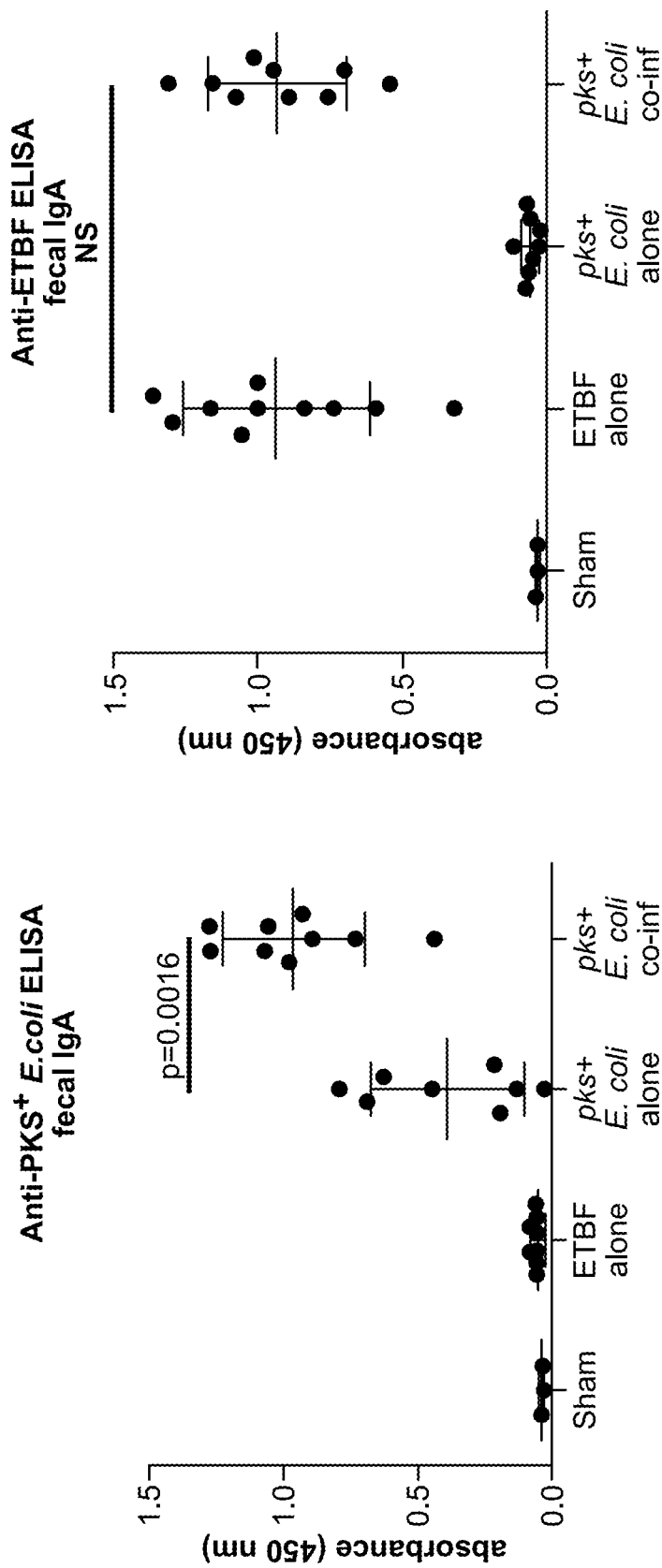
FIGS. 4A-4D show that ETBF enhances pks+ E. coli colonization and colonic epithelial cell damage.

Immunohistochemistry (IHC) quantification: Because no regional differences (proximal, mid, distal colon) in γH2AX staining were identified, six crypts were selected for γH2AX quantification from each mouse; 2 each from the proximal, middle, and distal mouse colon. Only crypts displaying proper colon surface to crypt cross-sectional orientation, permitting counting of all cells and those cells with γH2AX staining, were selected for quantification. Positive cells (containing 3 or more nuclear foci) were counted along with total number of cells in the crypt and a resulting percentage was determined. H2AX IHC staining shown for distal colon (FIG. 4D, FIG. 13). Quantified results display all crypts examined from 4-5 mice per condition at day four after AOM administration and bacterial inoculation (f FIG. 4D, FIGS. 13A, 13B). Cells were counted blinded by PF and CMD.

Statistical Analysis: Data were analyzed using the nonparametric unpaired, two-tailed Mann-Whitney U test for two group comparisons, nonparametric Kruskal-Wallis test for multiple group comparisons, log rank test or X2 tests as labeled for each figure. For multiple group comparison achieving statistical significance with Kruskal-Wallis testing, we then performed subsequent two group comparisons of biological interest using Mann-Whitney U testing. For assessment across the 6 cell groups displayed in FIG. 3E (see also FIGS. 15A, 15B), log-transformed data and two-way ANOVA was used to take into account cell types when comparing treatment groups. Data are presented as mean+/−s.e.m or as box-and-whisker plots where the line represents the median, the box the interquartile range and the whiskers, the tenth and ninetieth percentiles. P-values <0.05 were considered statistically significant.

Results

Figure 5:
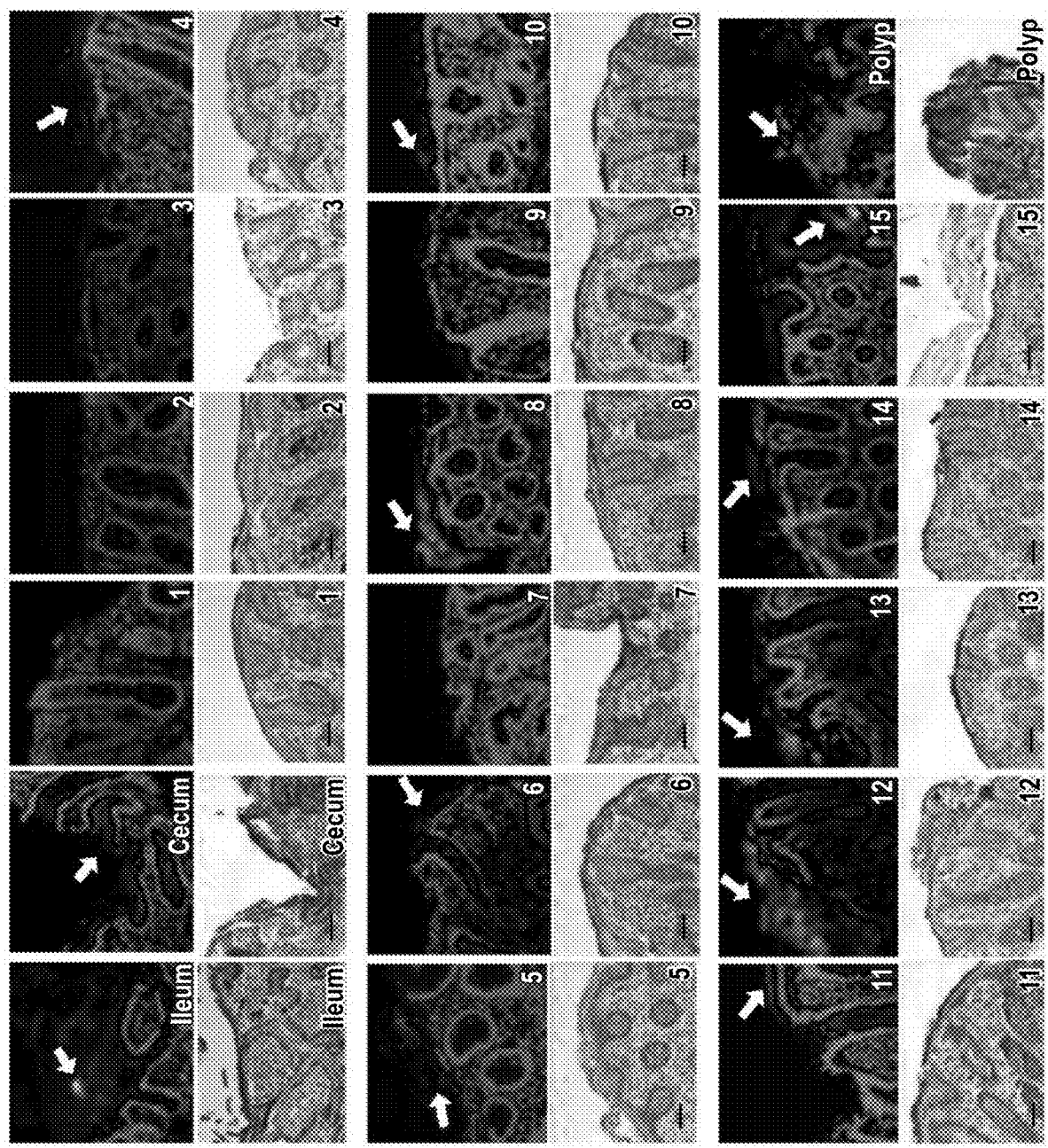
FIG. 5 shows representative all-bacteria FISH and PAS-stained histopathology images along the colonic axis of the FAP colon. Fluorescent in situ hybridization (FISH) of all bacteria (red) on colon specimens were collected from an individual with FAP (3775). Tissue specimens were collected approximately every 3-5 centimeters starting in the right colon (sample 1) and ending in the rectum (sample 15). Patchy biofilms (delineated by white arrows) detected throughout the colon on both polyp and grossly normal tissues. PAS-stained histopathology images for each FISH image are displayed. Images are representative of at least ten 5 μm sections examined per tissue specimen shown and were obtained at 40× magnification. Scale bar is 50 μm.
Figure 6:
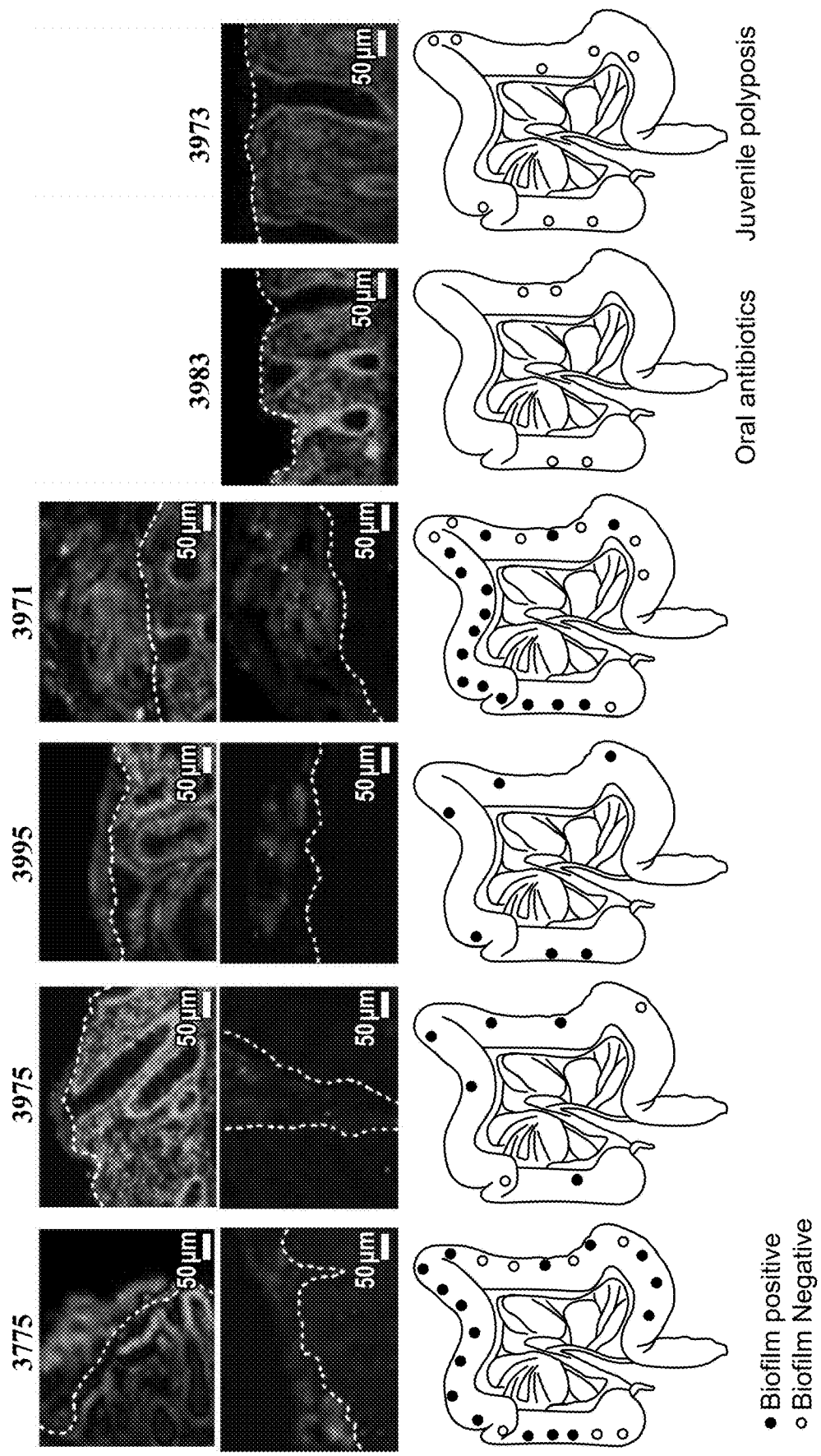
FIG. 6 shows the biofilm distribution and composition in FAP patients. Specimens from five prospectively collected FAP colons and one juvenile polyposis (JP) colon were available for FISH analysis. Colon tissue from four patients (3775, 3975, 3995 and 3971) contained a biofilm, while the JP and antibiotic-treated patient colon tissues had no biofilms. FISH of all bacteria (red) top panels, displaying representative biofilms from each patient and species specific FISH probes (below) of E. coli (red) and B. fragilis (green) biofilm composition from each patient. Bottom panel displays colon specimen sites with biofilm designations (red=biofilm, blue=no biofilm). Images are representative of n=4-23 tissue samples per patient screened (at least ten 5 μm sections screened per patient). Images were obtained at 40× magnification. Scale bar is 50 μm.

Surgically resected tissues preserved in Carnoy's fixative from five patients with FAP and one with juvenile polyposis syndrome were initially screened (Table 1). Colon biopsies from individuals undergoing screening colonoscopy or surgical resections served as controls (n=20, Table 2). Polyps and macroscopically normal tissue were labeled with a panbacterial 16S ribosomal RNA (rRNA) fluorescence in situ hybridization (FISH) probe. Each FAP patient exhibited bacterial invasion through the mucus layer scattered along the colonic axis (FIG. 1A, Table 3, FIG. 5). Unlike the continuous mucosal bio-films in sporadic CRC patients (6), FAP tissue displayed patchy bacterial mucus invasion (average length, 150 μm) on approximately 70% of the surgically resected colon specimens collected from four of six hereditary tumor patients. Biofilms were not restricted to polyps, nor did they display right colon geographic preference as observed in sporadic CRC (Table 3 and FIGS. 5 and 6). Bio-films were not detected in the mucus layer of the FAP patient who received oral antibiotics 24 hours before surgery (Table 1 and FIG. 6).

Specimens with bacterial biofilms were further screened by additional 16S rRNA probes to recognize the major phyla detected in biofilms of sporadic CRC; namely, *Bacteroides/Prevotella*, Proteobacteria, Lachnospiraceae, and Fusobacteria. Notably, FAP biofilms were composed predominantly of mucus-invasive Proteobacteria (about 60 to 70%) and *Bacteroides* (10 to 32%) (Table 3). Fusobacteria were not detected, and Lachnospiraceae were rare (<3%) by quantitative FISH analysis (Table 3).

Figure 7:
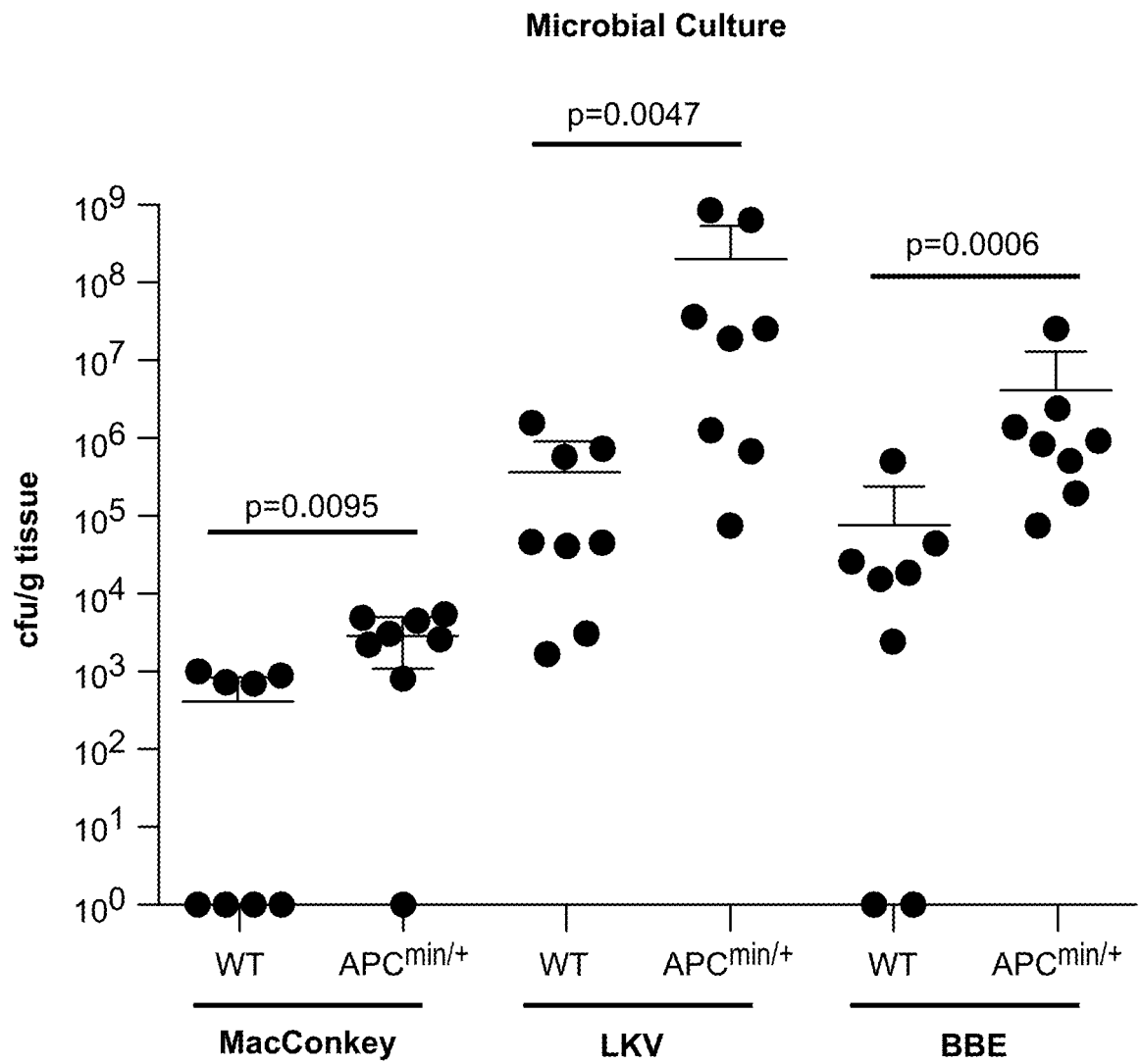
FIG. 7 shows the colonic mucosal colonization of ApC$^{Min\Delta716/+}$ vs wild-type (C57B1/6) mouse littermates. Microbiology culture analysis of distal colon mucosal tissues from 6-week old wild-type C57B1/6 (n=8) and Apc$^{Min\Delta716/+}$ (n=8) mouse littermates (2 litters). Apc$^{Min\Delta716/+}$ mice displayed significantly more cultivatable Enterobacteriaceae (MacConkey), Gram-negative obligate anaerobes (Brucella laked blood agar with kanamycin and vancomycin, LKV) and B. fragilis group (BBE) than their WT littermates. Data displayed as colony-forming units per gram of tissue cultured (8 mice per group, mean+/−SEM) and significance was calculated using the Mann-Whitney U test.

Additional probe sets (Table 4) identified the predominant biofilm members as *E. coli* and *B. fragilis* (FIG. 1A, bottom panels; Table 3). Invasion of the epithelial cell layer by biofilm community members was detected in all patients harboring biofilms (FIG. 1B), a finding similar to that in sporadic CRC patients. Further, FISH of mucosal biopsies from ileal pouches or anorectal remnants of additional, longitudinally followed, postcolectomy FAP patients revealed biofilms in 36% and mucosal-associated *E. coli* or *B. fragilis* in 50% (table S5). Thus, *E. coli* and *B. fragilis* are frequent, persistent mucosal colonizers of the FAP gastrointestinal tract. Of note, semiquantitative colon mucosa bacterial cultures of $Apc^{M\Delta716}/+$ mice (truncation at the 716 codon of Apc), a murine correlate of FAP, displayed similar enrichment of *Bacteroides* and Enterobacteriaceae compared to wild-type (WT) littermates, consistent with data reported for $ApC^{Min\Delta850/+}$ mice (FIG. 7) (8). These results provide evidence that Apc mutations enhance mucosal bacterial adherence, altering the bacterial—host epithelial interaction.

Figures 1C, 1D:
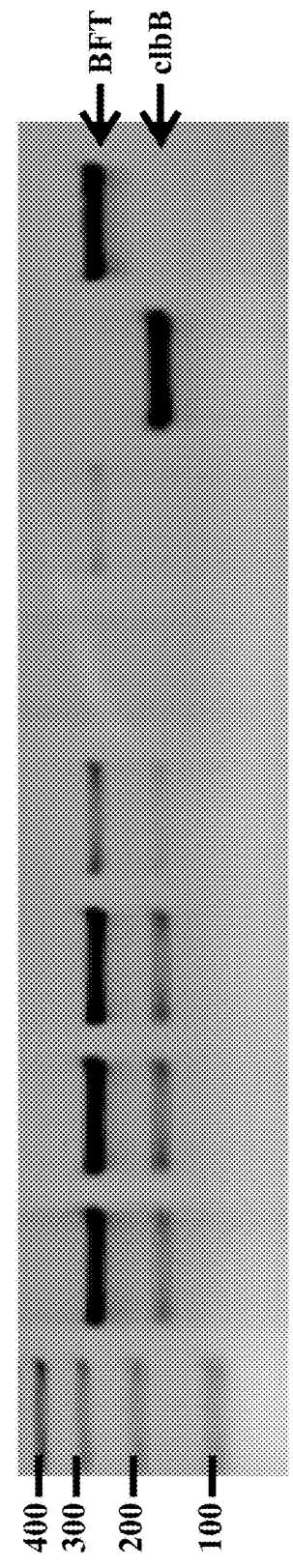

Molecular subtypes of both *E. coli* and *B. fragilis*, were the two dominant biofilm members identified in direct contact with host colon epithelial cells in the FAP patients tested. *E. coli* containing the polyketide synthase (pks) genotoxic island (encodes the genes responsible for synthesis of the colibactin genotoxin) induces DNA damage in vitro and in vivo along with colon tumorigenesis in azoxymethane (AOM)—treated interleukin-10 (IL-10)— deficient mice (10), whereas, enterotoxigenic *Bacteroides fragilis* (ETBF) induces colon tumorigenesis in $Apc^{Min/+}$ mice (9). Human epidemiological studies have associated ETBF and pks+ *E. coli* with inflammatory bowel disease and sporadic CRC (10-13). Thus, banked frozen mucosal tissues were cultured from 25 FAP patients (two polyps and two normal tissues per patient when available, Table 1) and 23 healthy individuals (mucosal sample from surgical resection or one ascending and one descending colon biopsy per colonoscopy subject, Table 2) for the presence of pks+ *E. coli* and ETBF. The mucosa of FAP patients was significantly associated with pks+ *E. coli* (68%) and ETBF (60%) compared to healthy subject mucosa (22% pks+ *E. coli* and 30% ETBF) (FIG. 1C). There was no preferential association of ETBF or pks+ *E. coli* with polyp or normal mucosa from FAP patients. Typically, mucosal samples from individual patients were concordant for pks+ *E. coli* or ETBF (73% for pks+ *E. coli,* 59% for ETBF), similar to results for mucosal bft detection in sporadic CRC patients (13). Notably, pks+ *E. coli* and ETBF mucosal co-association occurred at a higher rate (52%) than expected to occur randomly (40.8%) given the frequencies for the individual species (FIG. 1C). Increased mucosal coassociation also occurred in healthy control subjects (22% observed versus 6.6% expected) (FIG. 1C). Laser capture micro-dissection of mucosal biofilms from the initial FAP patients (FIG. 6 and Table 1) contained both bft and clbB as determined by polymerase chain reaction (PCR) analysis, indicating that the carcinogenic subtypes of *B. fragilis* and *E. coli*, respectively, were present in the mucus layer in direct contact with the FAP epithelium (FIG. 1D). In contrast, neither virulence gene was detected in the mucus layer of control subject 3760 whereas bft was detected in the mucus layer of control subject 3730, consistent with the culture analysis of this sample (FIG. 1D) (13).

The high frequency of pks+ *E. coli* and ETBF co-colonization in FAP colons highlights the importance of understanding the potential effects of simultaneously harboring these two carcinogenic bacteria. Consequently, two murine models, AOM treatment without DSS (see materials and methods) and $Apc^{Min\Delta716/+}$ mice were used to test the hypothesis that pks+ *E. coli* and ETBF cocolonization enhances colon tumorigenesis compared to monocolonization with either bacterium. The rate of spontaneous colon tumorigenesis is very low in both model systems.

Figure 2B:
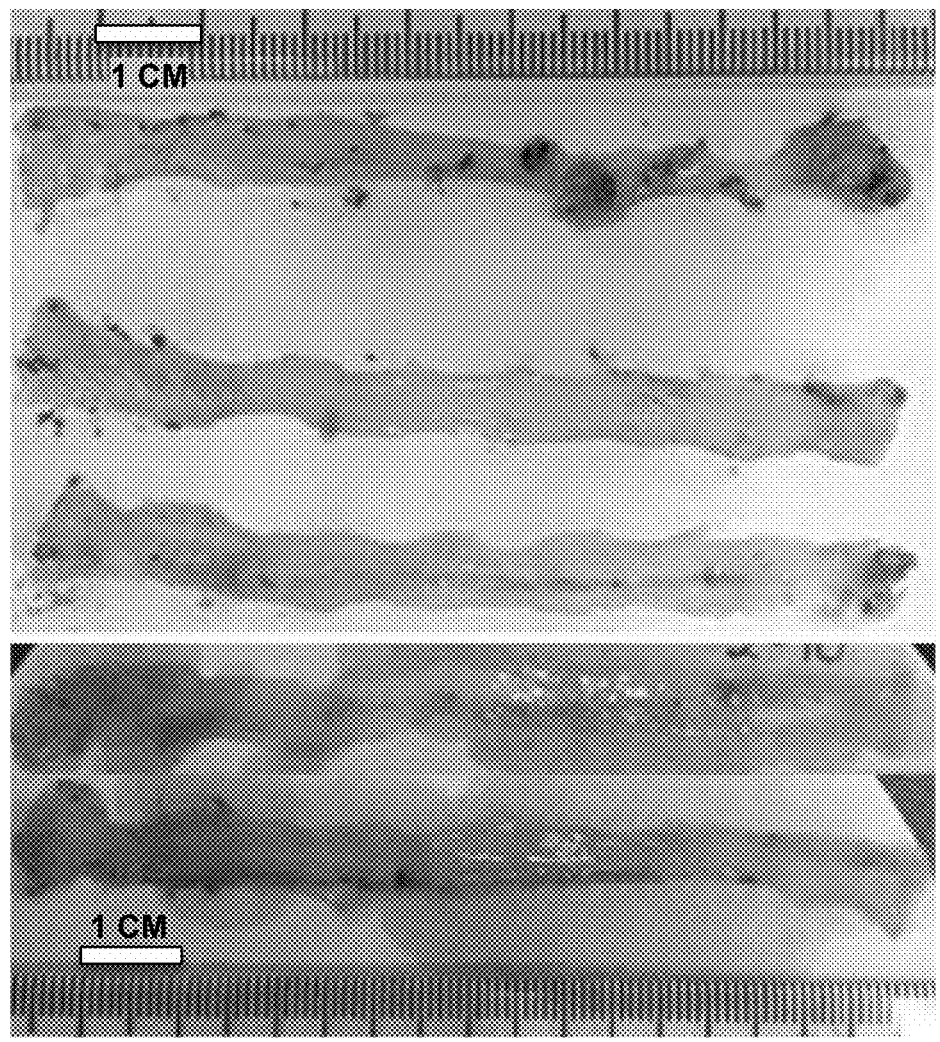
Figure 2C:
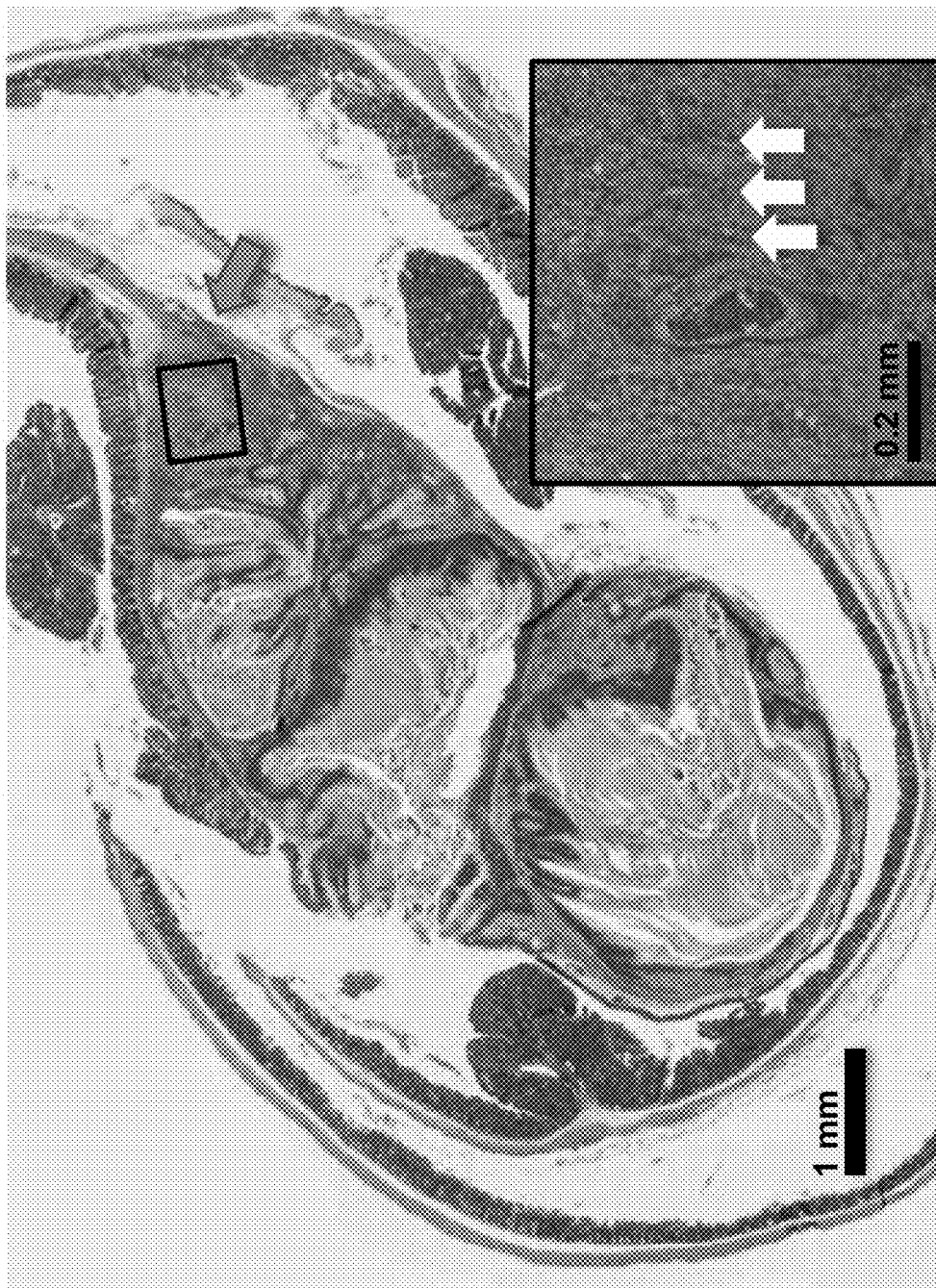

Specific pathogen-free wild-type mice were treated with the carcinogen AOM and mono-inoculated or co-inoculated with canonical strains of pks+ *E. coli* (the murine adherent and invasive strain, NC101) and ETBF (strain 086-5443-2-2) (9, 10). Fecal ETBF or pks+ *E. coli* colonization was similar under mono-colonization or co-colonization conditions, persisting until colon tumor formation was assessed at 15 weeks after colonization (FIG. 8). Mono-colonized (pks+ *E. coli* or ETBF) mice displayed few to no tumors. However, pronounced tumor induction occurred in co-colonized mice, including an invasive cancer, providing evidence for the requirement for both bacteria to yield oncogenesis (FIGS. 2A to 2C). Tumorigenesis required the presence of BFT and the colibactin genotoxin as in-frame deletions of the bft gene and the pks virulence island significantly decreased tumors (FIG. 2A).

Figure 2D:
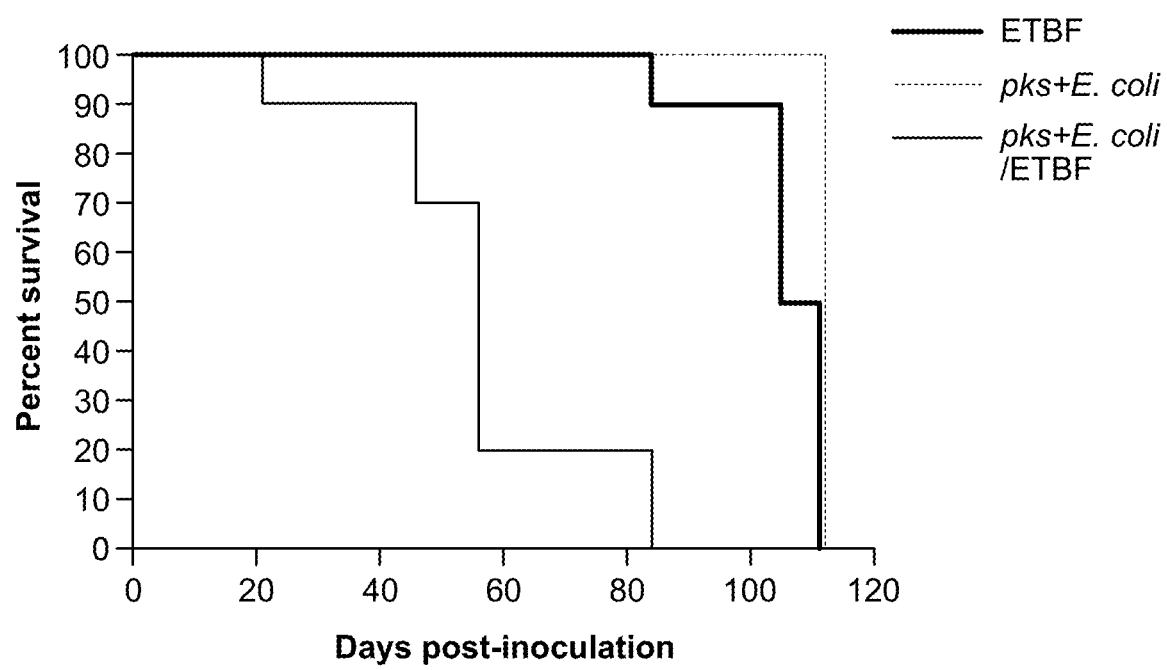
Figure 9A:
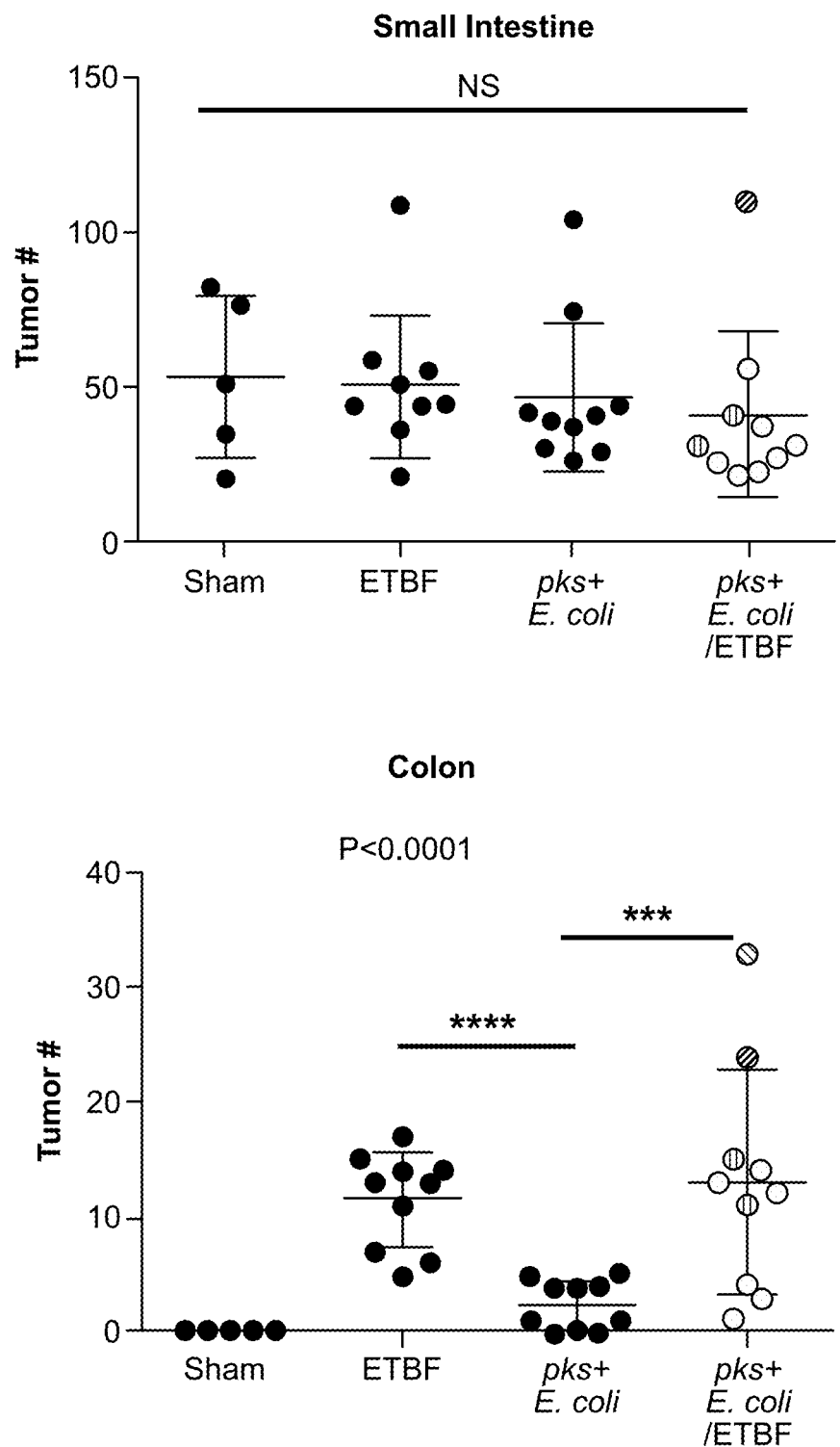
FIGS. 9A, 9B show the Apc$^{Min/+}$ mouse tumor quantification and colon inflammation scores in mono- and co-colonized mice. Gross tumor counts (FIG. 9A) and inflammation colon scores (FIG. 9B) of 12 week Apc$^{Min\Delta716/+}$ sham (n=5), and mice mono-colonized with pks+ E. coli (n=10), ETBF (n=10) or co-colonized with pks+ E. coli/ETBF (n=10; mortality time points noted; only 2 co-colonized mice survived to 12 weeks). No significant difference was detected between mice mono-colonized with ETBF and co-colonized with pks+ E. coli/ETBF in gross small intestinal tumors (NS, non-significant). Data represent mean+/−SEM of 3 independent experiments. Overall significance was calculated using the Kruskal-Wallis test and the overall p values are shown; Mann-Whitney U was used for two group comparisons, p values: *, p<0.006; **, p<0.0001.
Figure 9B:
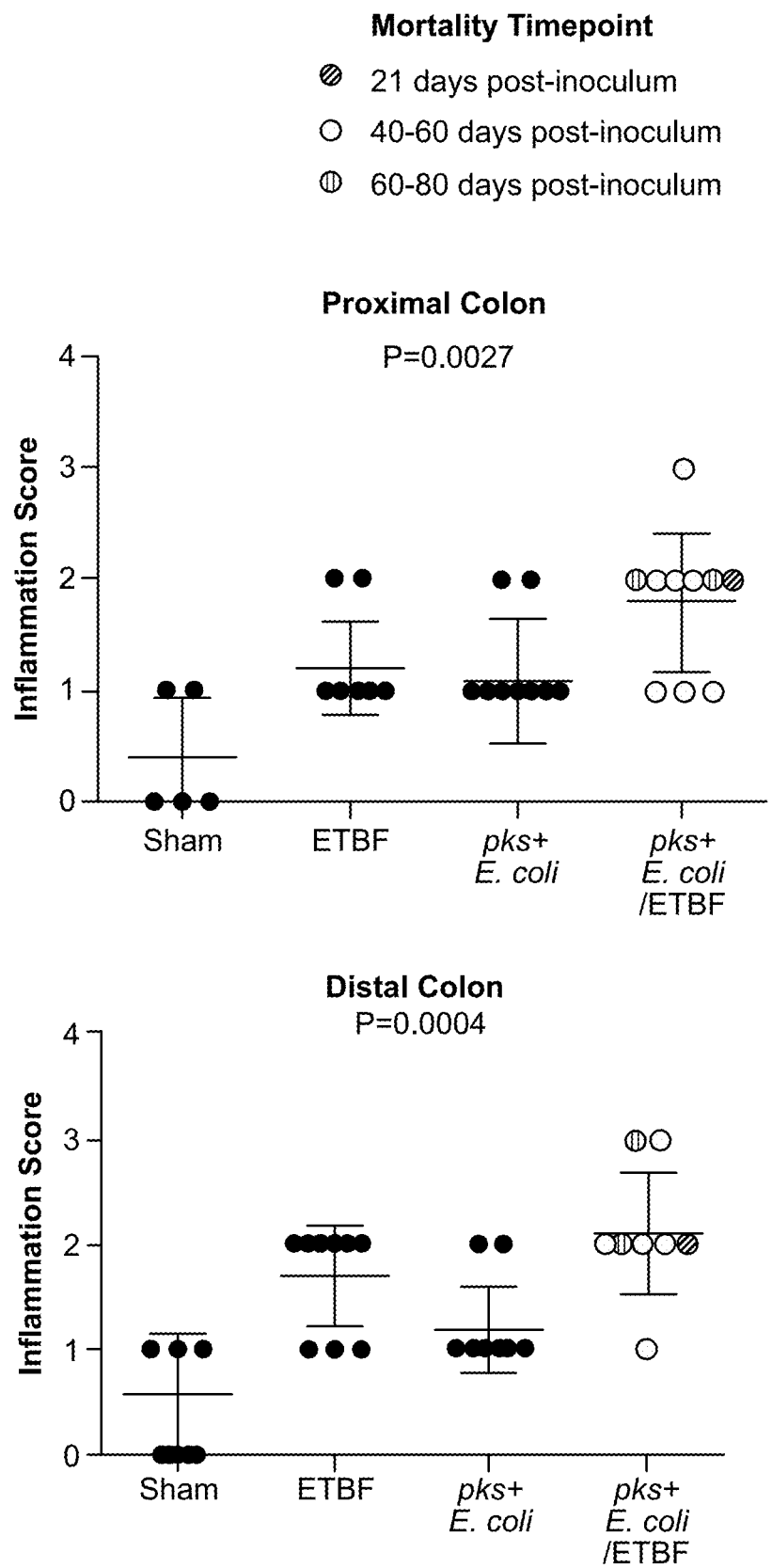

$Apc^{Min\Delta716/+}$ mice co-colonized with ETBF and pks+ *E. coli* exhibited enhanced morbidity with rapid weight loss and significantly increased mortality (P<0.0001) [loss of 80% of the mice (n=8) by 8 weeks and the remaining 20% (n=2) at 12 weeks after colonization]. In contrast, 90% (n=9) and 100% (n=10) of mice mono-colonized with ETBF or pks+ *E. coli*, respectively, survived 15 weeks after colonization (FIG. 2D). The robust tumorigenesis of ETBF alone (at 15 weeks) and co-colonized mice (majority deceased by 8 weeks after colonization) was similar, whereas tumor numbers were significantly increased in the co-colonized cohort compared to pks+ *E. coli* alone (FIGS. 9A, 9B). Notably, at early time points, inflammation was increased in the co-colonized cohort compared to either ETBF or pks+ *E. coli* alone (FIGS. 9A, 9B). Together these results provide evidence that the significant increase in colon inflammation and early tumorigenesis in the co-colonized mice contributed to their earlier mortality in the Apc$^{Min/+}$ mouse model.

Figure 3A:
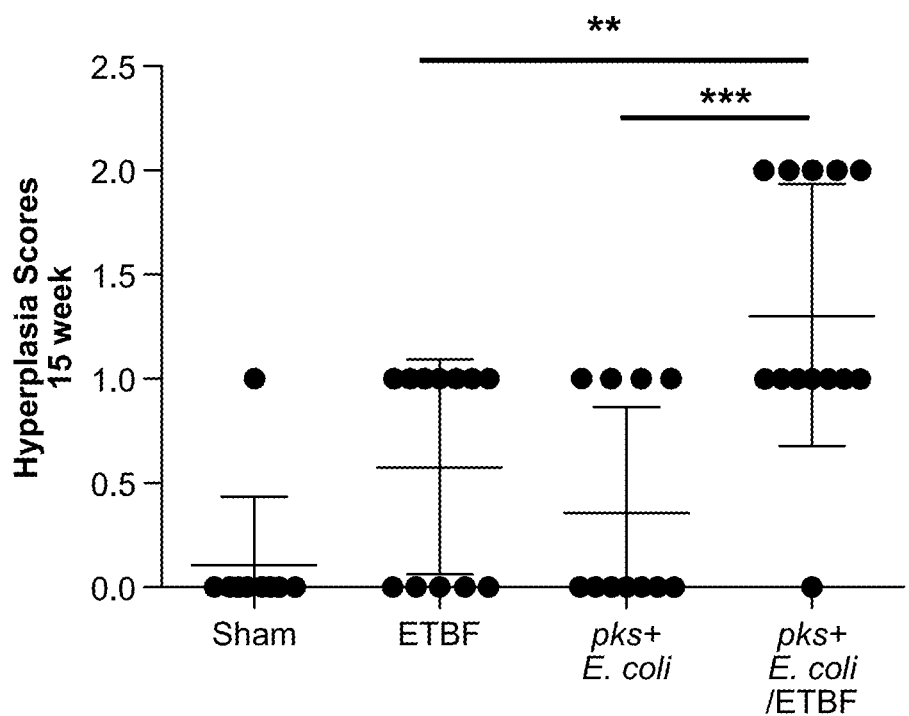
FIGS. 3A-3E show that IL-17—induced inflammation is necessary for bacterial-driven tumorigenesis.
Figure 3B:
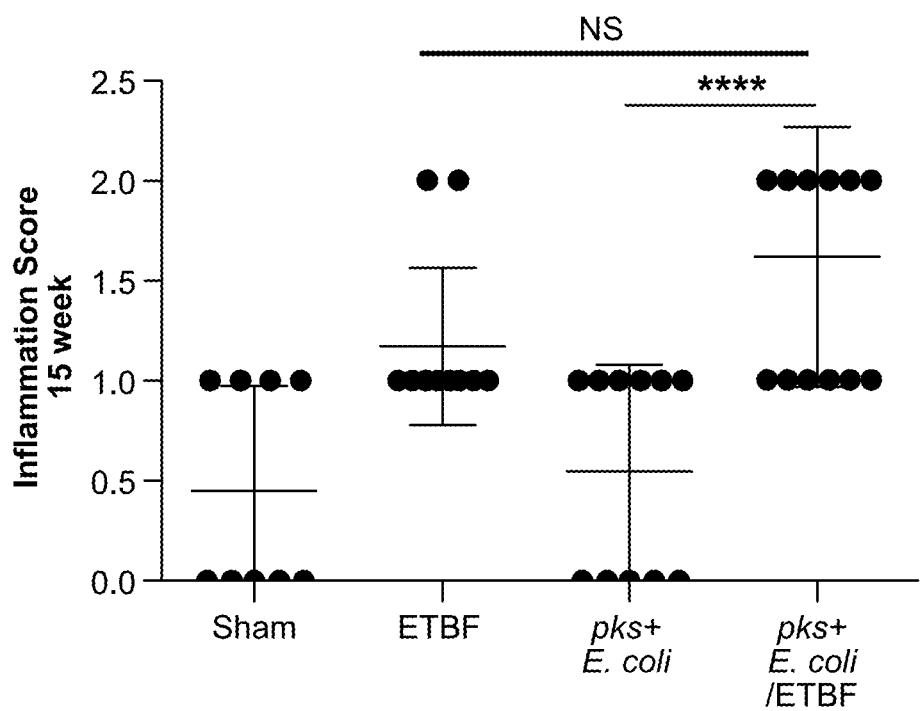
Figure 3C:
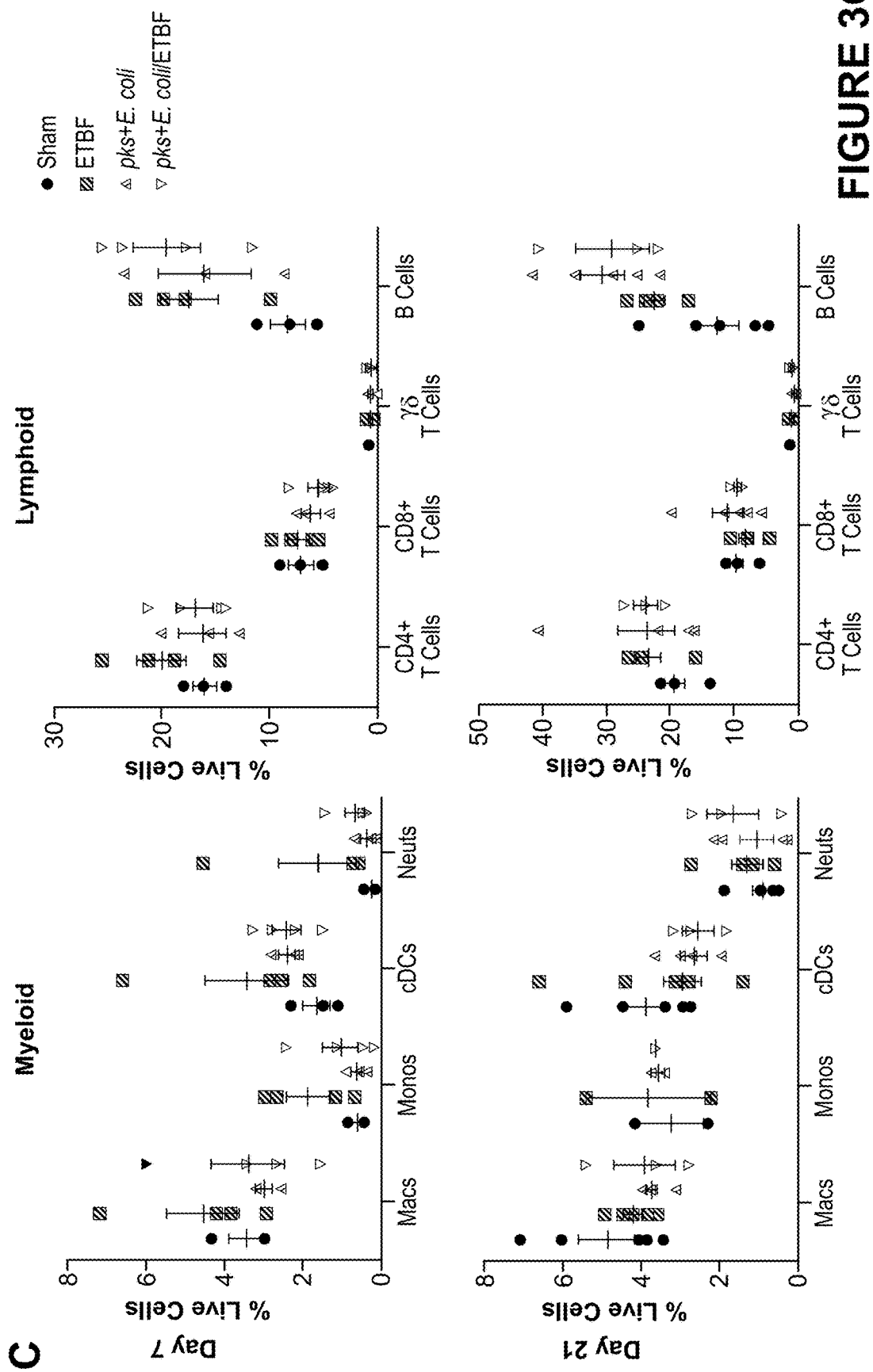
Figures 10A, 10B:
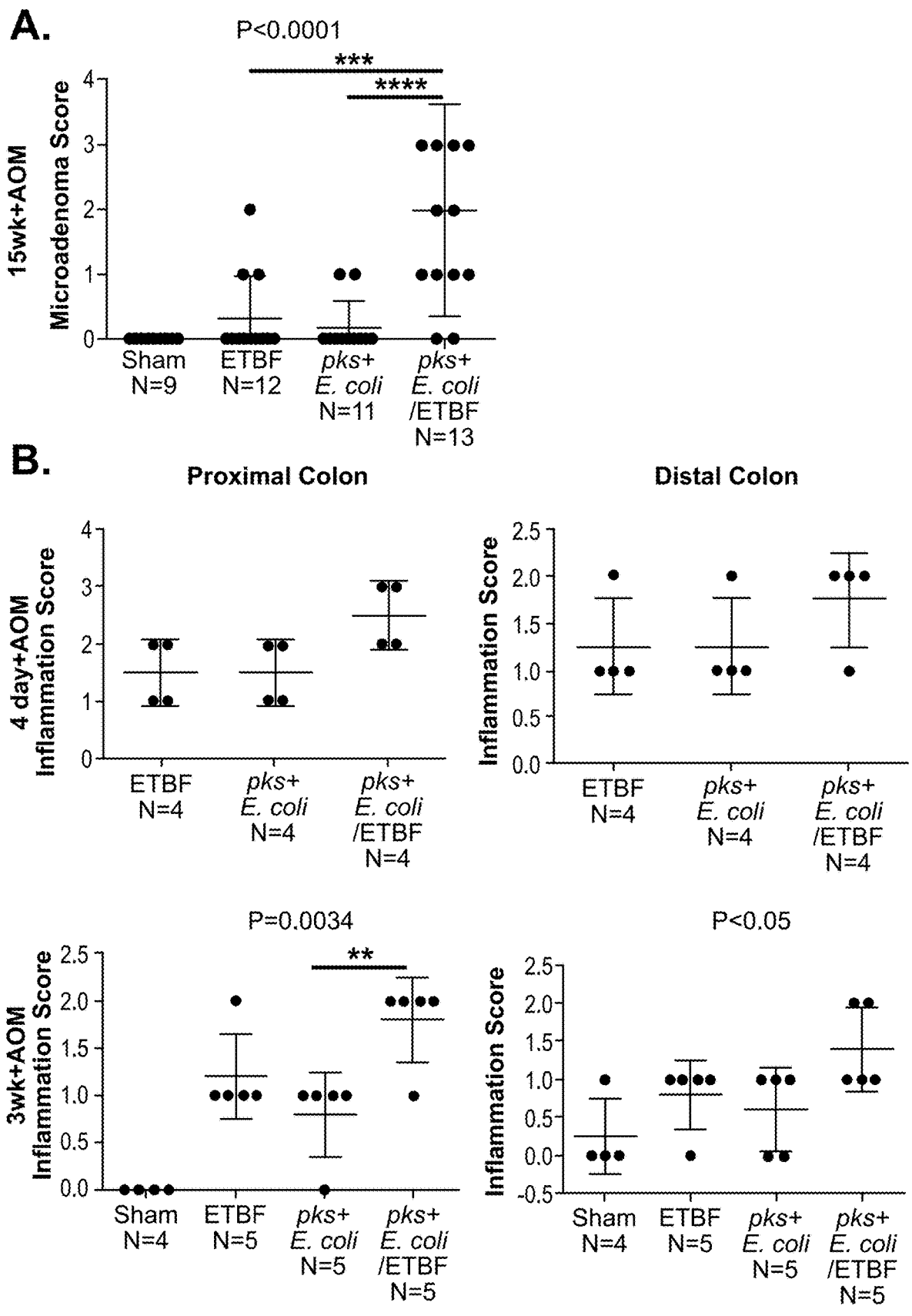
FIGS. 10A and 10B show the microadenomas and colon inflammation scores of wild-type AOM mice. Histopathology microadenoma (FIG. 10A) and inflammation (FIG. 10B) scores of AOM mice mono-colonized with pks+ E. coli or ETBF and co-colonized with pks+ E. coli/ETBF. At 15 weeks post-inoculation, microadenomas (FIG. 10A) were significantly increased under co-colonization conditions. For (FIG. 10B), no significant difference was noted between colonization groups at 4-days (top panel) in either the proximal (left panel) or distal (right panel) colons. At 3-weeks (bottom panel) post inoculation, inflammation was significantly increased in both proximal colon (left panel) and distal colon (right panel). For FIG. 10A, data represent mean+/−SEM of 3 independent experiments (total 9-13 mice per group). For FIG. 10B (top), data represent mean+/−SEM of one independent experiment (total 4 mice per group). For FIG. 10B (bottom), data represent mean+/−SEM of 2 independent experiments (total 4-5 mice per group). For FIGS. 10A and 10B, overall significance was calculated using the Kruskal-Wallis test and the overall p value is shown; Mann-Whitney U was used for two group comparisons, p values: , p=0.04; *p<0.002; ****p=0.0006.

Consistent with enhanced tumorigenesis, histopathological analysis revealed significantly increased colon hyperplasia and mucosal micro-adenomas in co-colonized AOM-treated mice compared to mono-colonized mice (FIGS. 3A and 10A). However, histopathology scoring revealed modest differences in inflammation over time (4 days to 15 weeks) in mono- and co-colonized AOM mice (FIG. 3B and FIG. 10B). Thus, overall inflammation did not seem to explain differential tumor induction. To determine if the type of inflammation contributed to differences in tumorigenesis, lamina propria immune-cell infiltrates of mono-colonized and co-colonized wild-type AOM mice were analyzed by flow cytometry. The general lymphoid panel revealed a marked B cell influx across all colonization groups (FIG. 3C) but no significant differences in the proportion of infiltrating T cells (CD4, CD8, or γδT cells) and myeloid populations between monocolonized and cocolonized AOM mice (FIG. 3C) either at the acute (1-week) or chronic (3-week) stage of infection.

Figure 3D:
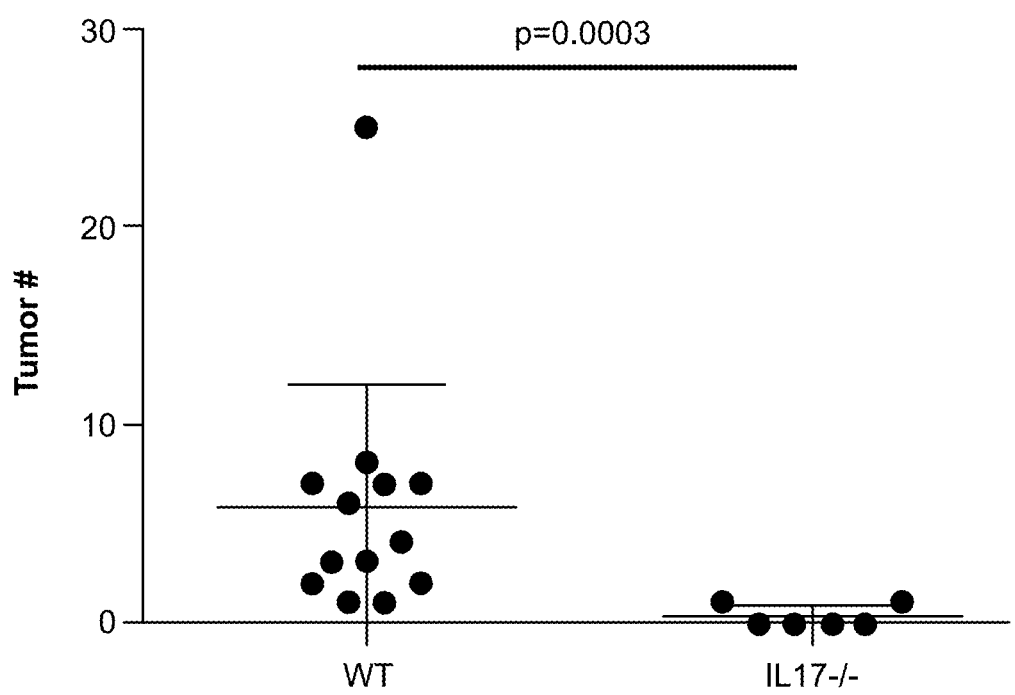
Figure 3E:
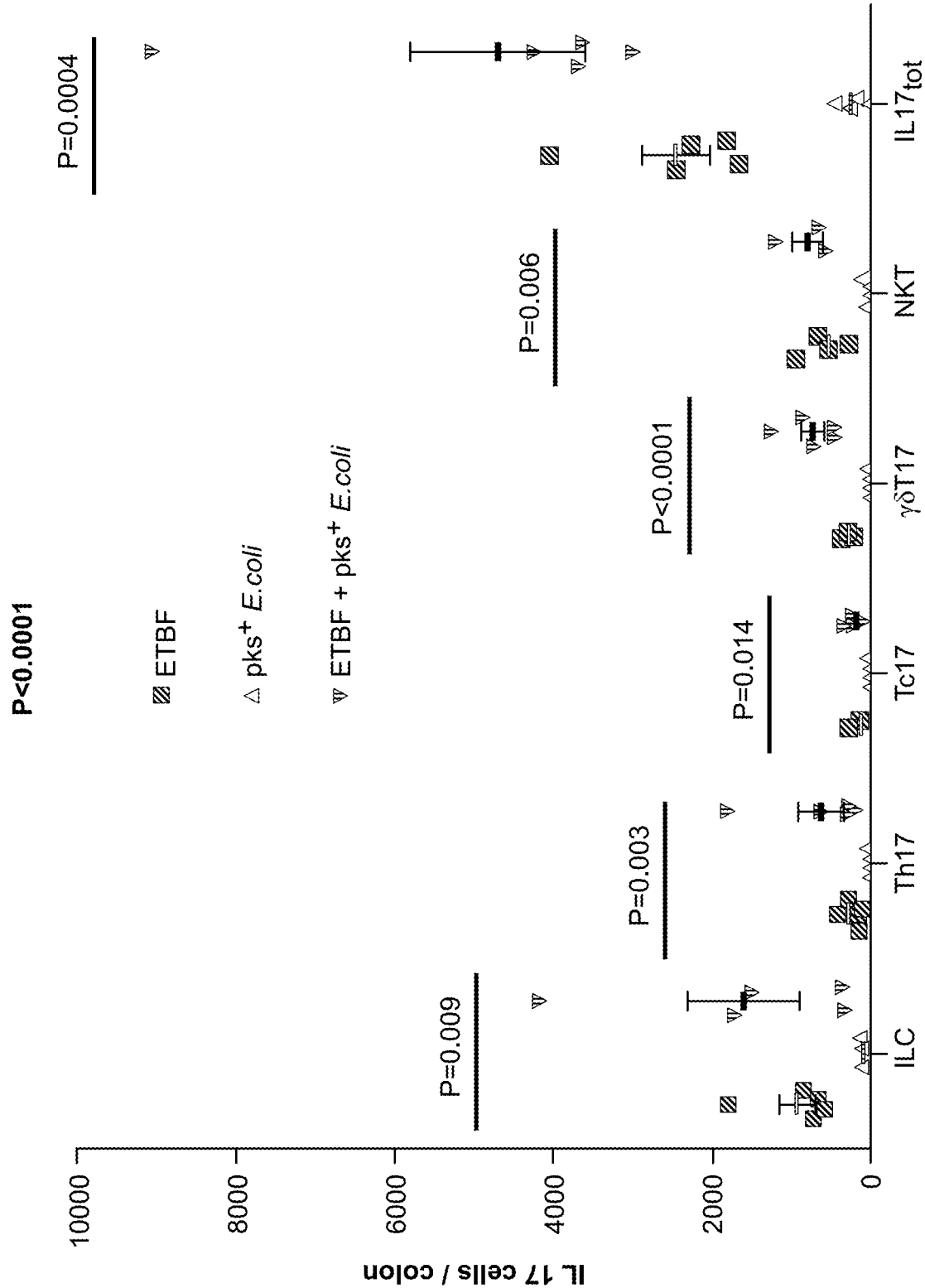
Figure 11:
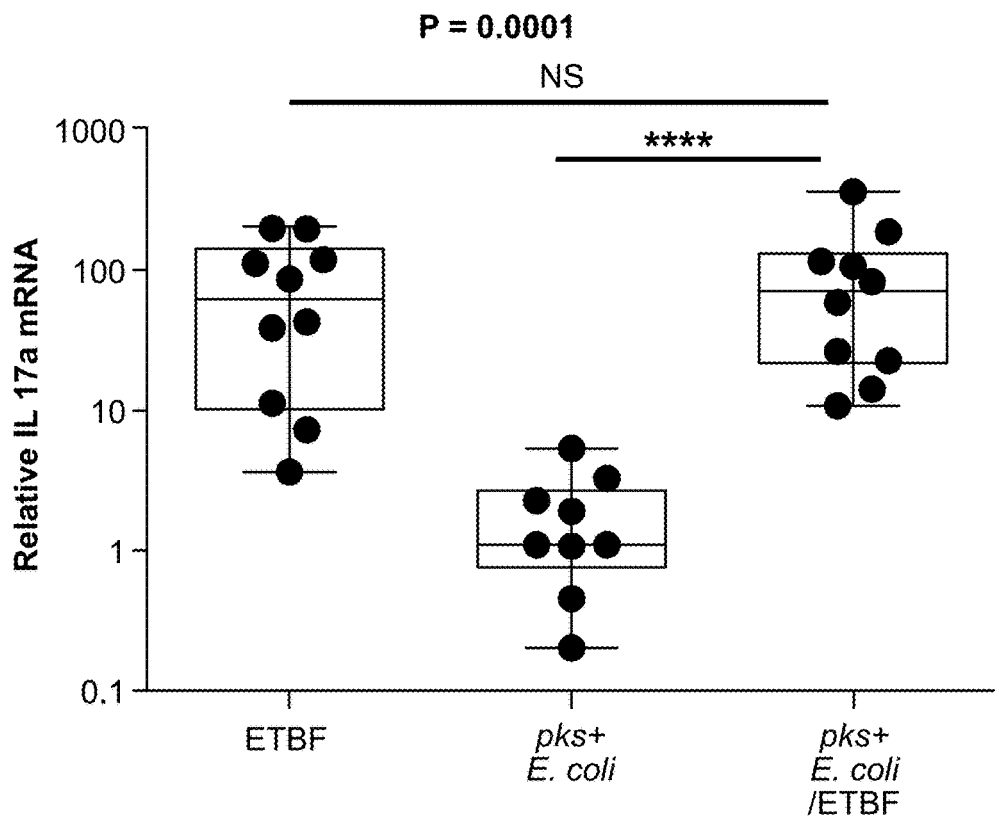
FIG. 11 shows the distal colon mucosal IL-17 mRNA expression mono-colonized and co-colonized AOM mice. Distal colon normal (non-tumor) mucosal IL-17 mRNA expression relative to sham in ETBF and pks+ E. coli mono-colonized and co-colonized AOM mice at 15 weeks. Data represent box-and-whisker plot (line, median; box, interquartile range; whiskers, $10^{th}$ and $90^{th}$ percentiles) of 3 independent experiments (total 9-10 mice per group). Overall significance was calculated using the Kruskal-Wallis test and the overall p value is shown; Mann-Whitney U was used for two group comparisons, p value: ****, P<0.0001. NS=non-significant.

Of particular interest was IL-17, as the tumorigenic potential of ETBF in Apc$^{MinΔ716/+}$ mice has been attributed, in part, to IL-17 (9). Because bft was necessary for synergistic tumor induction under co-colonization conditions (FIG. 2A), the role of IL-17 in the co-colonized AOM model was tested. Although IL-17 expression analysis by quantitative PCR revealed no significant difference in overall mucosal IL-17 mRNA levels between 15-week ETBF mono-colonized and ETBF and pks+ E. coli co-colonized mice (FIG. 11), co-colonization of IL-17—deficient AOM mice ablated tumorigenesis (FIG. 3D). To specifically test whether ETBF and pks+ E. coli co-colonization affected early colon mucosal IL-17 production, germ-free C57BL/6 mice were mono- or co-colonized and innate and adaptive lymphocyte subsets analyzed by flow cytometry. Germ-free mice co-colonized with ETBF and pks+ E. coli displayed a trend toward increase in total mucosal IL-17-producing cells when compared to mono-colonized ETBF or pks+ E. coli mice, driven by both adaptive [T helper 17 ($T_H$17)] and innate (particularly γδT17) cells (FIG. 3E and Table 7). Although necessary for tumorigenesis (FIG. 3D), IL-17 alone appears insufficient to explain synergistic tumorigenesis in co-colonized mice because robust IL-17 induction by ETBF mono-colonization (FIG. 11) induced only meager colon tumorigenesis in AOM mice (FIG. 2A).

Because the general lymphoid panel revealed a marked B cell influx across all colonization groups (FIG. 3C), the secretory immunoglobulin A (IgA) response was profiled by IgA enzyme-linked immunosorbent assay (ELISA) using stool collected 4 weeks after colonization from AOM mice. Co-colonized mice had a significantly more robust IgA response to pks+ E. coli than mice mono-colonized with pks+ E. coli, whereas the fecal anti-ETBF IgA response was similar under mono- and co-colonization conditions (FIG. 4A). Thus, the increased fecal IgA response was specific to pks+ E. coli in mice co-colonized with ETBF, providing evidence that co-colonization enhanced mucosal exposure to pks+ E. coli.

Figure 4B:
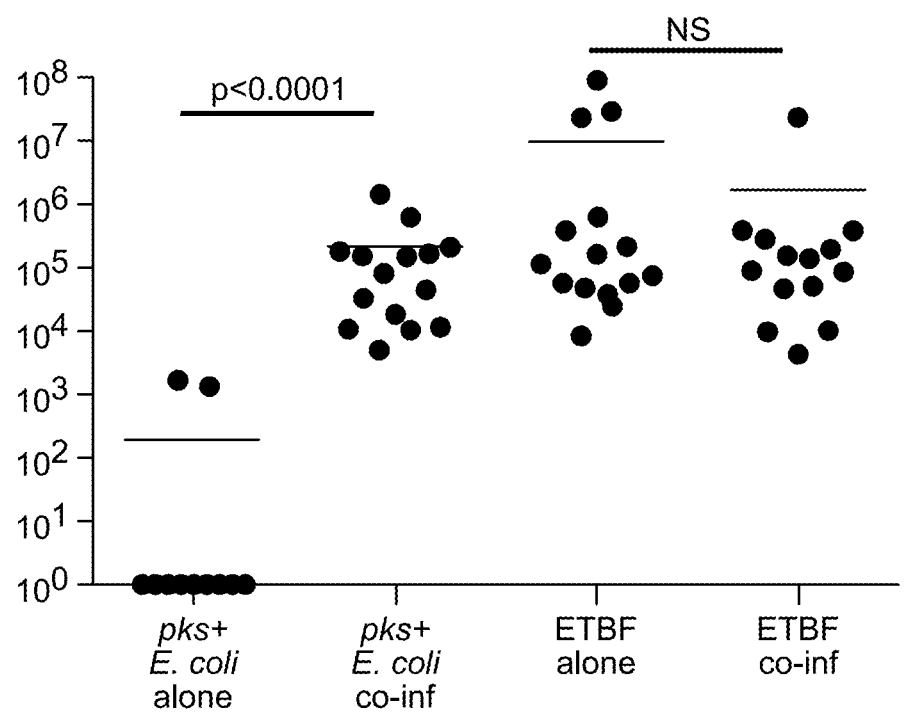
Figure 4C:
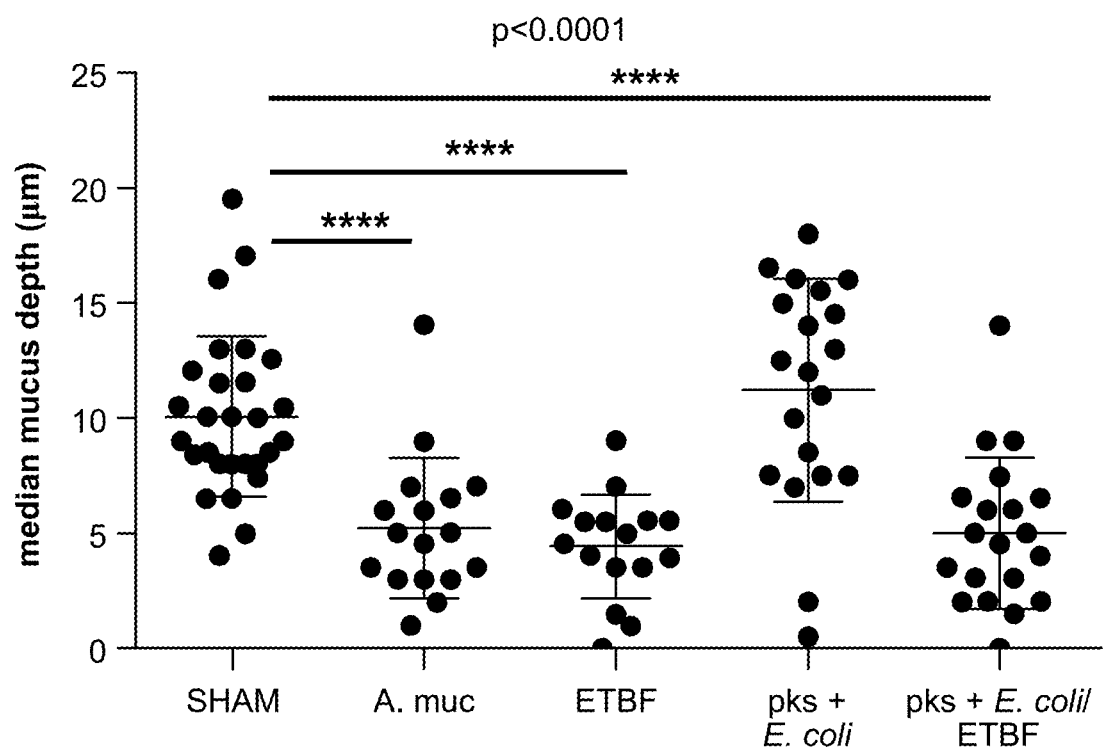
Figure 4D:
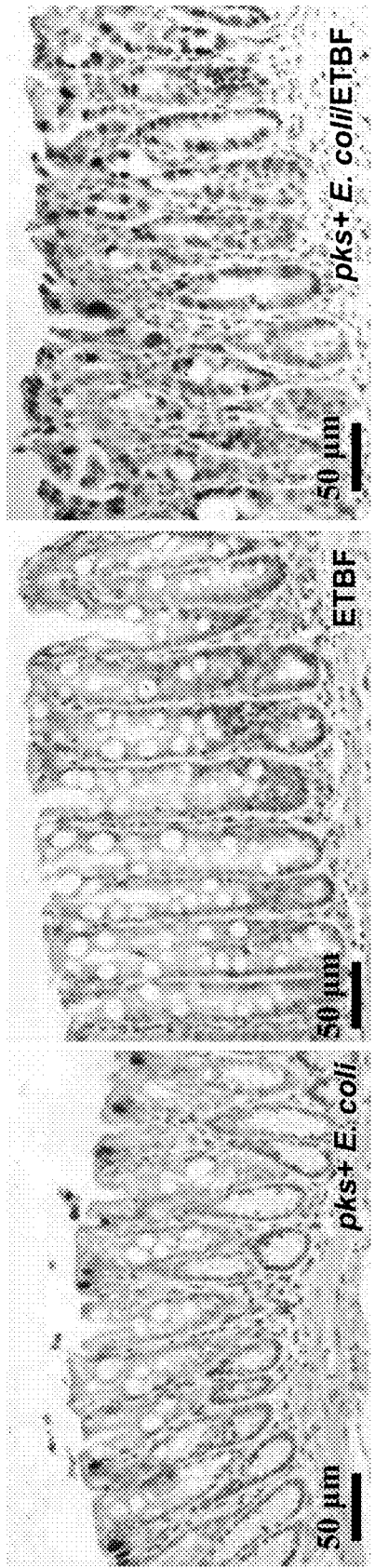
Figure 4D:
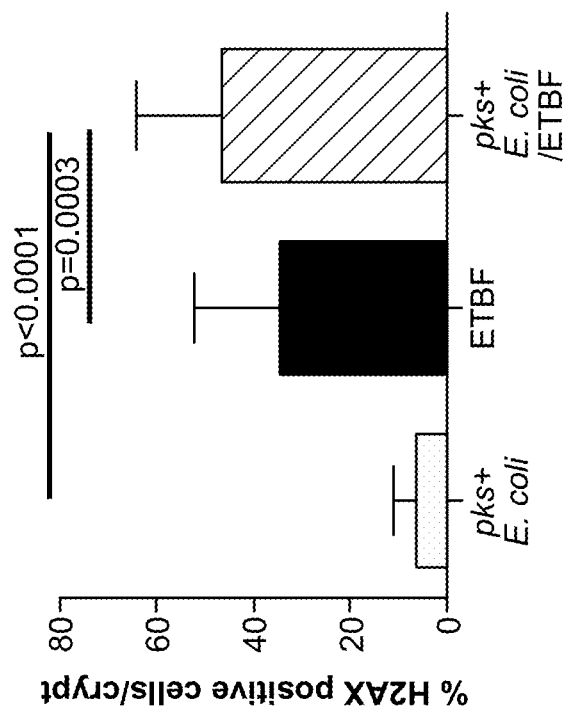
Figure 12:
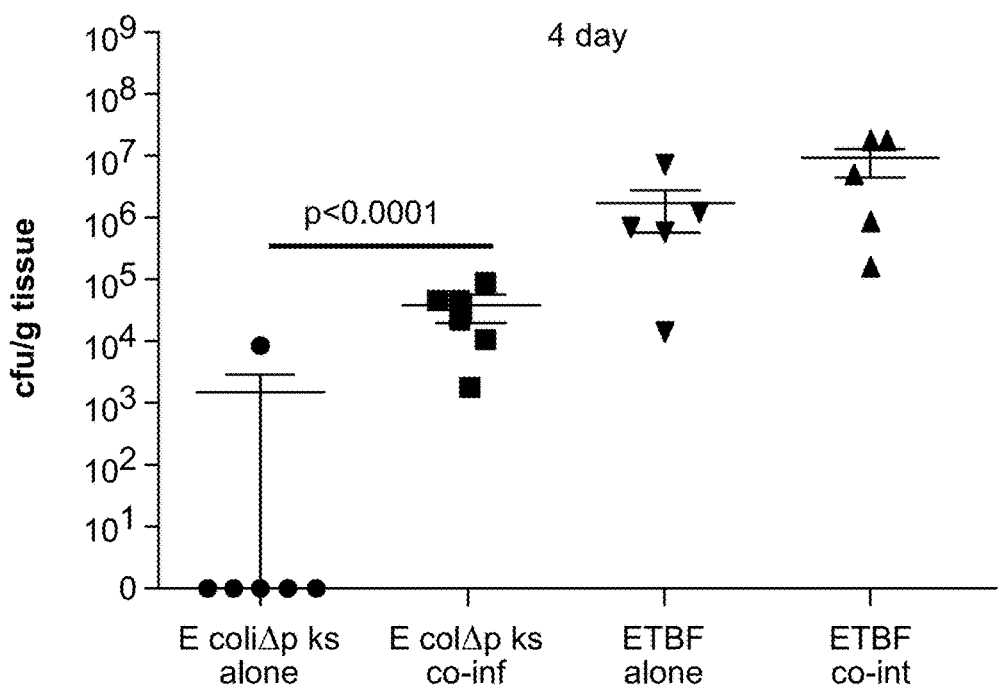
FIG. 12 shows the mucosal colonization of E. coli Δpks and ETBF in AOM mice. Mucosal colonization is enhanced for E. coli Δpks under co-colonization conditions in AOM mice. Mucosal colonization is displayed as colony-forming units (cfu) per gram of tissue. Data represent mean+/−SEM of one independent experiment (total 5-6 mice per group). Significance was calculated using the Mann-Whitney U test.

Although fecal colonization of both pks+ E. coli and ETBF was equivalent under both mono- and co-colonization conditions (FIG. 8), quantification of mucosal-adherent ETBF and pks+ E. coli revealed a marked increase in mucosal-adherent pks+ E. coli under co-colonization conditions compared to pks+ E. coli mono-colonization (FIG. 4B). Hence, under mono-colonization conditions, pks+ E. coli is largely cultivatable only from the colon lumen whereas in the presence of ETBF, pks+ E. coli colonizes the mucosa at high levels (103 to 10$^6$ colony-forming units per gram of tissue). Using Muc-2—producing HT29-MTX-E12 monolayers in vitro, the impact of pks+ E. coli and ETBF was tested on mucus. Although pks+ E. coli colonization alone had no impact on mucus depth, monolayer colonization with ETBF alone or cocolonized with pks+ E. coli significantly reduced mucus depth similar to colonization with A. muciniphila, a known human colonic mucin-degrading bacterium (FIG. 4C). These results provide evidence that mucus degradation by ETBF promotes enhanced pks+ E. coli colonization. Such a shift in the bacterial niche of pks+ E. coli would facilitate the delivery of colibactin, the DNA-damaging toxin released by pks+ E. coli, to colon epithelial cells. Consistent with this hypothesis, γ-H2AX immunohistochemistry revealed significantly enhanced DNA damage in the colon epithelial cells of AOM mice cocolonized with pks+ E. coli and ETBF compared to monocolonized (pks+ E. coli or ETBF) mice (FIG. 4D). Further, mice co-colonized with ETBF and E. coli$^{ΔPks}$ displayed similarly enhanced mucosal colonization with the E. coli strain (FIG. 12) but reduced tumors and no increase in DNA damage or IL-17 (FIG. 2A and FIGS. 13A and 13B, respectively). Lastly, persistent co-colonization of AOM-treated mice with the mucin-degrading A. muciniphila and pks+ E. coli did not enhance, but rather reduced, the modest colon tumorigenesis (FIGS. 14A and 14B) induced by pks+ E. coli mon-ocolonization. These results evidence that mucus degradation alone was insufficient to promote pks+ E. coli colon carcinogenesis in AOM mice.

Taken together, these data provide evidence that co-colonization with ETBF and pks+E. coli, found in more than half of FAP patients (in contrast to less than 25% of controls), promotes enhanced carcinogenesis through two distinct but complementary steps: (i) mucus degradation enabling increased pks+ E. coli adherence, inducing increased colonic epithelial cell DNA damage by colibactin (FIG. 4D and FIGS. 13A and 13B); and (ii) IL-17 induction promoted, primarily, by ETBF with early augmentation by pks+ E. coli co-colonization (FIGS. 3D and 3E, and Table 7). It is proposed herein, that together these mechanisms yield cooperative tumor induction in AOM mice co-colonized with ETBF and pks+ E. coli.

ETBF and pks+ E. coli commonly colonize young children worldwide. Thus, the results provide evidence that persistent co-colonization in the colon mucosa from a young age may contribute to the pathogenesis of FAP and potentially even those who develop sporadic CRC because APC loss or mutation occurs in the vast majority of sporadic CRC. It was noted that pks+ E. coli are phenotypic and genotypic adherent and invasive E. coli (AIEC) (14). Despite this designation, derived primarily from in vitro cell culture experiments, the canonical pks+ E. coli strain (NC101) used in these experiments was only cultivatable from the colon lumen in the absence of concomitant ETBF colonization in our mouse model. This ETBF-dependent shift to marked mucosal pks+ E. coli colonization is consistent with the observations that ETBF and pks+ E. coli co-colonize FAP colon biofilms, where both bacteria invade and cocolonize the mucus layer throughout the FAP colon. These findings provide evidence that analysis of coexpression of bft and clbB have value in general screening and potential prevention of CRC.

TABLE 1

Table 1 FAP patient metadata

| Patient ID | Age | Sex | Race | Operation | Mutation | Analyses |
|---|---|---|---|---|---|---|
| 365 | 39 | M | Caucasian | Proctocolectomy | ND | Microstructure |
| 1420 | 16 | F | Caucasian | Colectomy | ND | Microstructure |
| 1679 | 27 | F | Caucasian | Colectomy | ND | Microstructure |
| 2017 | 8 | F | Caucasian | Proctocolectomy | ND | Microstructure |
| 2215 | 16 | M | Caucasian | Proctocolectomy | ND | Microstructure |
| 2544 | 7 | F | Caucasian | Proctocolectomy | ND | Microstructure |
| 2732 | 25 | F | Caucasian | Proctocolectomy | ND | Microstructure |
| 2735 | 35 | M | Caucasian | Proctocolectomy | ND | Microstructure |
| 2891 | 65 | F | African American | Partial Proctocolectomy | ND | Microstructure |
| 2904 | 18 | F | Caucasian | Proctocolectomy | ND | Microstructure |
| 2927 | 22 | M | Caucasian | Proctocolectomy | ND | Microstructure |
| 3024 | 53 | M | Caucasian | Proctocolectomy | ND | Microstructure |
| 3026 | 38 | M | Caucasian | Proctocolectomy | ND | Microstructure |
| 3037 | 9 | M | Caucasian | Proctocolectomy | ND | Microstructure |
| 3166 | 43 | F | Caucasian | Proctocolectomy | ND | Microstructure |
| 3174 | 17 | F | Caucasian | Colectomy | ND | Microstructure |
| 3233 | 27 | M | African American | Proctocolectomy | ND | Microstructure |
| 3345 | 35 | F | Caucasian | Colectomy | ND | Microstructure |
| 3381 | 25 | M | Caucasian | Proctocolectomy | ND | Microstructure |
| 3775* | 51 | F | Caucasian | Colectomy | MYH | Seq, FISH, Microstructure |
| 3971 | 27 | M | African American | Proctocolectomy | ND | Seq, FISH, Microstructure |
| 3973*[a] | 27 | F | Caucasian | Colectomy | ND | Seq, FISH, Microstructure |
| 3975 | 50 | M | Caucasian | Colectomy | APC | Seq, FISH, Microstructure |
| 3983[b] | 51 | F | African American | Colectomy | APC | Seq, FISH, Microstructure |
| 3995 | 39 | M | Caucasian | Proctocolectomy | APC | Seq, FISH, Microstructure |

Abreviations: ND, not determined, micro = aerobic and anaerobic microbiology culture (see methods);
FISH = flourescent in situ hybridization
*attenuated phenotype
[a]juvenile polyposis
[b]Patient received oral antibiotics 24 hours prior to surgery

TABLE 2

Table 2: Control Subject metadata

| Patient ID | Age | Sex | Race | Analyses |
|---|---|---|---|---|
| 3714 | 33 | F | Caucasian | Microstructure |
| 3723 | 49 | F | Caucasian | Microstructure |
| 3724 | 66 | M | Hispanic | Microstructure |
| 3730 | 61 | F | Caucasian | Seq, FISH, Microstructure |
| 3734 | 57 | F | Caucasian | Seq, FISH, Microstructure |
| 3737 | 52 | F | Caucasian | Seq, FISH, Microstructure |
| S55 | 60 | F | African American | Seq, FISH, Microstructure |
| S56 | 52 | F | African American | Seq, FISH, Microstructure |
| S57 | 52 | M | Caucasian | Seq, FISH, Microstructure |
| S58 | 57 | F | African American | Seq, FISH, Microstructure |
| S59 | 77 | M | African American | Seq, FISH, Microstructure |
| S60 | 45 | F | Caucasian | Seq, FISH, Microstructure |
| S61 | 58 | M | Caucasian | Seq, FISH, Microstructure |
| S62 | 64 | M | African American | Seq, FISH, Microstructure |
| S63 | 74 | F | African American | Seq, FISH, Microstructure |
| S64 | 61 | M | African American | Seq, FISH, Microstructure |
| S65 | 67 | F | African American | Seq, FISH, Microstructure |
| S66 | 49 | F | African American | Seq, FISH, Microstructure |
| S67 | 67 | F | Caucasian | Seq, FISH, Microstructure |
| S68 | 47 | F | African American | Seq, FISH, Microstructure |
| S69 | 57 | M | Caucasian | Seq, FISH, Microstructure |
| S70 | 59 | F | Caucasian | Seq, FISH, Microstructure |
| S71 | 52 | F | African American | Seq, FISH, Microstructure |

Abbreviations: Micro = as set forth in Table 1; FISH - as set forth in Table 1

TABLE 3

FISH Analysis of Bacterial Biofilms on FAP Mucosa

| Patient ID | # Tissue samples Collected | #Samples with Biofilms | Bacterial Biofilm Location | Biofilm Density | Gammaproteobacteria & Betaproteobacteria (% of b f population) |
|---|---|---|---|---|---|
| 3775* | 23 | 16.69% | 3 Right (1 polyp. 22.60E+11 paired normal) 13 left (1 polyp, 12 paired normal) | | 67% |

TABLE 3-continued

| | | | | | |
|---|---|---|---|---|---|
| 3971 | 22 | 14.61% | 4 Right (1 polyp. 11 left (2 polyps, 9 paired normal) | 38.02E+10 | 59% |
| 3975 | 7 | 5.71% | 1 Right (polyp) 4 left (2 polyps, 2 paired normal) | 2.80E+11 | 69% |
| 3995 | 6 | 6.100% | 3 Right (1 polyp. 3 left (2 polyps, 1 paired normal) | 26.40E+11 | 64% |
| 3973* [a] | 8 | 0 | NA | NA | NA |
| 3983 [b] | 4 | 0 | NA | NA | NA |

| Patient ID | Bacteroides (% of b f population) | Lachnospiraceae (% of b f population) | Fusobacteria (% of b f population) | E. coli (% of b f population) | B. fragilis (% of b f population) |
|---|---|---|---|---|---|
| 3775* | 12% | 3% | 0% | 49% | 9% |
| 3971 | 32% | 2% | 0% | 51% | 29% |
| 3975 | 10% | 0% | 0% | 66% | 7% |
| 3995 | 11% | 3% | 0% | 59% | 5% |
| 3973* [a] | NA | NA | NA | NA | NA |
| 3983 [b] | NA | NA | NA | NA | NA |

TABLE 4

Table 4: FISH Probes

| Probe Target(s) | Probe Name | Fluorophore | Probe Sequence (5'-3') | Reference |
|---|---|---|---|---|
| Kingdom Bacteria except Plancromycetales and Verrucombicrobia | Eub338 | Cy3, Alexa 405 | GCTGCCTCCCGTAGGAGT | 1 |
| Fusobacteria | | Alexa 488 | GGCTTCCCCATCGGCATT | 2 |
| Prevotella, Bacteroides | PRV392 | Rhodamine Red X | GCACGCTACTTGGCTGG | 3 |
| Bacteroidetes (Bacteroides, Parabacteroides, Prevotella) | CFB286 | Alexa 514 | TCCTCTCAGAACCCCTAC | 4 |
| Betaproteobacteria | Bet42a | Alexa 647 | GCCTTCCCACTTCGTTT | 5 |
| Gammaproteobacteria | Gem42a | Alexa 647 | GCCTTCCCACATCGTTT | 5 |
| Lachnospiraceae | Lac435 | Tesas Red X | TCTTCCCTGCTGATAGA | 6 |
| Enterobacteriaceae except Proteus spp | Ent186 | Alexa 555 | CCCCCWCTTTGGTCTTGC | 7 |
| Bacteroides fragilis | S-S-Bfrag-998-a-A20 | Alexa 633 | GTTTCCACATCATTCCACTG | 8 |
| Escherichia coli | Eco1531 | HRP-tyamide488 | CACCGTAGTGCCTCGTCATCA | 9 |
| Escherichia coli | Eco1161 | HRP-tyamide488 | GCATAAGCGTCGCTGCCG | 10 |

TABLE 5

Table 5:

| Patent | Colonoscopy time point | Biofilm | E. Coli | Bacteroides fragilis |
|---|---|---|---|---|
| 1 | 1 | + | + | + |
| | 2 | + | + | − |
| | 3 | + | − | + |
| 2 | 1 | + | + | − |
| | 2 | + | + | − |
| | 3 | − | − | − |

TABLE 5-continued

Table 5:

| Patent | Colonoscopy time point | Biofilm | E. Coli | Bacteroides fragilis |
|---|---|---|---|---|
| 3 | 1 | + | + | − |
|   | 2 | − | + | + |
|   | 3 | + | + | − |
| 4 | 1 | + | + | − |
| 5 | 1 | − | − | − |
| 6 | 1 | − | − | − |
| 7 | 1 | − | − | − |
| 8 | 1 | − | − | − |
|   | 2 | − | + | − |
| 9 | 1 | − | − | − |
| 10 | 1 | − | − | − |
| 11 | 1 | − | − | − |
|   | 2 | + | + | + |
| 12 | 1 | − | − | − |
| 13 | 1 | − | − | − |
|   | 2 | − | + | − |
| 14 | 1 | − | − | − |

Colonoscopy time points represents serial numbering of colon mucosa over 16 months in post-colectomy FAP patients.

TABLE 6

| Primer target | Primer Name | Sequence(5'-3') | Reference | Product size (bp) |
|---|---|---|---|---|
| Akkermansia muciniphila 16S (Taqman) (FIG. S10) | AM1(S-St-Muc-1129-a-a-20] | CAGCACGTGAAGGTGGGGAC | 11 | NA |
|  | AM2[S-St-Muc-1129-a-a-20] | CCTTGCGGGTTGGCTTCAGAT |  |  |
|  | A. muc 16S Probe | HEX]ACTGGGCATTGTAGTACGTGTGCA | This Study |  |
| E. Coli pks (Taqman) (FIG. S10) | clbB-F | GCGCATCCTCAAGAGTAAATA | 12 | NA |
|  | clbB-R | GCGCTCTATGCTCATCAACC |  |  |
|  | pks Probe | FAM]TATTCGACACAGAACAACGCCGGT[BHQ1] | This Study |  |
| E. coli pks (FIG. 1D) | clbB-F | GCAACATACTCGCCCAGCT | This Study | 163 |
|  | clbB-R | TCTCAAGGCGTTGTTGTTTG |  |  |
| B. fragilis toxin (bft) (FIG. 1D) | bft-F | GCGAACTCGGTTTATGCAGT | This Study | 280 |
|  | bft-R | GTTGTAGACATCCCACTGGC |  |  |

TABLE 7

Table 7: P-value of Mann-Whitney test (FIG. 3E)

| Comparasion | ILC | Th17 | Tc17 | Yδ T17 | NKT | IL-17 tot |
|---|---|---|---|---|---|---|
| ETBF vs. pks + E. coli | 0.0159 | 0.0159 | 0.0571 | 0.0159 | 0.0159 | 0.0159 |
| Pks + E. coli vs. co-infection | 0.0159 | 0.0159 | 0.0159 | 0.0159 | 0.0571 | 0.0159 |
| ETBF vs. Co-infection | >0.9999 | 0.2222 | 0.5556 | 0.0079 | 0.3929 | 0.0556 |

REFERENCES

E. R. Fearon, B. Vogelstein, Cell 61, 759-767 (1990).
F. M. Giardiello et al., *Gastroenterology* 106, 1542-1547 (1994).
C. Dejea, E. Wick, C. L. Sears, *Future Microbiol.* 8, 445-460 (2013).
A. Swidsinski et al., *Gut* 56, 343-350 (2007).
A. Swidsinski, V. Loening-Baucke, A. Herber, *J. Physiol. Pharmacol.* 60 (Suppl 6), 61-71 (2009).
C. M. Dejea et al., *Proc. Natl. Acad. Sci. U.S.A.* 111, 18321-18326 (2014).
C. H. Johnson et al., *Cell Metab.* 21, 891-897 (2015).
J. S. Son et al., *PLOS ONE* 10, e0127985 (2015).
S. Wu et al., *Nat. Med.* 15, 1016-1022 (2009).
J. C. Arthur et al., *Science* 338, 120-123 (2012).
T. P. Prindiville et al., *Emerg. Infect. Dis.* 6, 171-174 (2000).
M. Prorok-Hamon et al., *Gut* 63, 761-770 (2014).
A. Boleij et al., *Clin. Infect. Dis.* 60, 208-215 (2015).
M. Martinez-Medina et al., *J. Clin. Microbiol.* 47, 3968-3979 (2009)
K. J. Rhee, S. Wu, X. Wu, D. L. Huso, B. Karim, A. A. Franco, S. Rabizadeh, J. E. Golub, L. E. Mathews, J. Shin, R. B. Sartor, D. Golenbock, A. R. Hamad, C. M. Gan, F. Housseau, C. L. Sears, Induction of persistent colitis by a human commensal, enterotoxigenic *Bacteroides fragilis*, in wild-type C57BL/6 mice. *Infect. Immun.* 77, 1708-1718 (2009). doi:10.1128/IA1.00814-08 Medline.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

What is claimed:

1. A method of treating colorectal cancer in a subject, comprising administering a therapeutically effective amount of one or more agents which are bactericidal, bacteriostatic and/or inhibit growth or activity of bacteria in a bacterial biofilm in the subject's gastrointestinal tract, wherein the bacterial biofilm comprises at least one bacterial type from

*Bacteroides* and at least one bacterial type from Enterobacteriaceae, wherein the at least one bacterial type from *Bacteroides* is enterotoxigenic *Bacteroides fragilis* (ETBF) and the at least one bacterial type from Enterobacteriaceae is *Escherichia coli* (*E. coli*); thereby treating the subject.

2. The method of claim 1, wherein the one or more agents which are bactericidal, bacteriostatic and/or inhibit growth or activity of bacteria comprise antibacterial agents, antibiotics, probiotics, mucosal protective agents, or combinations thereof.

3. The method of claim 1, wherein the *E. coli* comprise polyketide synthase (pks) genes.

4. The method of claim 1, wherein the *E. coli* encode or express a colibactin genotoxin.

5. The method of claim 1, wherein the ETBF and *E. coli* co-colonize the subject's gastrointestinal tract.

6. The method of claim 2, wherein the one or more antibiotics comprise: clindamycin, beta-lactams, macrolides, chloramphenicol, aminoglycosides, fluoroquinolones, carbapenems, sulbactam or combinations thereof.

7. The method of claim 1, wherein the administered one or more agents are B-cell activating factor (BAFF), cytokines, adjuvants, immunogens, peptides, vectors expressing one or more peptides, or combinations thereof.

8. The method of claim 7, wherein vectors expressing one or more peptides are administered and the peptides comprise one or more epitopes of ETBF and/or *E. coli*.

9. The method of claim 2, wherein the administered one or more agents are cytotoxic for ETBF and/or *E. coli*.

10. The method of claim 2, wherein the mucosal protective agents inhibit bacterial adherence to the subject's gastrointestinal tract.

11. The method of claim 2, wherein the administered one or more agents comprise an anti-cytokine agent that inhibits IL-17 induction by ETBF bacteria.

12. The method of claim 2, wherein the probiotic agent comprises *Bacteroides* Enterobacteriaceae, or the combination thereof.

13. The method of claim 1, further comprising administering to the subject a chemotherapeutic agent.

14. A method of preventing colorectal cancer or treating a subject for colorectal cancer, comprising administering to the subject an antimicrobial agent and/or probiotic, wherein colibactin (clbB) and *Bacteroides fragilis* toxin (bft) are detected in mucosa of a subject's gastrointestinal tract.

* * * * *